US012618616B2

(12) United States Patent
    Matthees

(10) Patent No.: US 12,618,616 B2
(45) Date of Patent: May 5, 2026

(54) HEATER SYSTEM FOR CATHETER MANUFACTURING

(71) Applicant: Edward John Matthees, Minneapolsi, MN (US)

(72) Inventor: Edward John Matthees, Minneapolis, MN (US)

( * ) Notice: Subject to any disclaimer, the term of this patent is extended or adjusted under 35 U.S.C. 154(b) by 555 days.

(21) Appl. No.: 18/220,613

(22) Filed: Jul. 11, 2023

(65) Prior Publication Data

US 2024/0019211 A1    Jan. 18, 2024

Related U.S. Application Data

(60) Provisional application No. 63/388,280, filed on Jul. 12, 2022.

(51) Int. Cl.
    *F27B 17/00*      (2006.01)
    *A61M 25/00*      (2006.01)
    *B29C 61/02*      (2006.01)

(52) U.S. Cl.
    CPC ..... *F27B 17/0083* (2013.01); *A61M 25/0009* (2013.01); *B29C 61/025* (2013.01); *A61M 2207/10* (2013.01)

(58) Field of Classification Search
    CPC ............ F27B 17/0083; A61M 25/0009; B29C 61/025
    See application file for complete search history.

(56) References Cited

U.S. PATENT DOCUMENTS 6,345,980 B1 * 2/2002 Tatarczuk ............... B25B 29/02
                                                  431/351
7,037,290 B2 * 5/2006 Gardeski ........... A61M 25/0158
                                                  604/95.01

* cited by examiner

*Primary Examiner* — Larry W Thrower

(74) *Attorney, Agent, or Firm* — Edwin E. Voigt, II

(57)                ABSTRACT

The invention is directed to a heating assembly for catheter manufacture which includes a heating element having a central vertical passage and a plurality of gas flow passages in communication with the central passage. The passages are at an angle relative to the central passage increasing heat transfer surface area. The invention may also include an iris assembly. The iris assembly includes a plurality of discs having slits which are offset relative to another disc. The invention may also include an insulation chamber surrounding the heating element. The flow of gas previously heated by the exterior of the thermos coupler and heating element is restricted by the insulation chamber for passage through the gas flow passages and into the central passage, so that the gas receives additional heat for exposure to sheathing material to be bound to a catheter.

17 Claims, 15 Drawing Sheets

HEATER SYSTEM FOR CATHETER MANUFACTURING

CROSS-REFERENCE TO RELATED APPLICATIONS

This application claims the benefit of U.S. Provisional Patent Application Ser. No. 63/388,280 filed Jul. 12, 2022 the entire contents of which being incorporated by reference herein in its entirety.

FIELD OF THE INVENTION

A heater assembly for the main tubular body of a medical catheter manufacturing device.

BACKGROUND

During the formation of the main tubular body of a medical catheter, a heating element is activated and drawn along a vertically disposed multi-layered catheter body. The heating element is used to heat shrink a polymer around the exterior of the main catheter body shaft as well as heating the multi-layers of the catheter body. The shrink polymer is not a component of the finished catheter its purpose is to transmit heat energy to and provide radial compression force to bond or reflow the multi layers of the finished catheter body forming a contiguous tube/catheter for future use in a medical procedure. The shrink polymer is removed after the catheter has been heat processed.

In the past some catheter manufacturing devices required that the inner heating element be cooled prior to a size exchange during the formation of a larger or smaller diameter catheter. The external stainless-steel component of the heating element for the known catheter manufacturing devices also served as an attachment point for the catheter manufacturing device and functioned as the interface between the resistive element heat source and thermo-couple mount, increasing alignment and quality control difficulties in alignment between the center line of the inside diameter of the heating element and the catheter body and sheathing material combination. The external stainless-steel component of the heating element for the known catheter manufacturing devices has a low coefficient of thermal conductivity and provides inefficient conductive heat transfer during the catheter formation process.

The known catheter manufacturing devices required a manual stabilization procedure after the loading of the components of the catheter body and sheathing material prior to the formation process. Also, the known catheter manufacturing devices were deficient in the stabilization and the centering of the catheter body and to the sheathing material relative to the heating unit prior to and during the catheter sheathing process.

In addition, the inner heating element for the known catheter manufacturing devices is relatively large with respect to the catheter being manufactured, resulting in inconsistencies in positioning, leading to non-uniform heating about the circumference and deviations in tolerances, adversely effecting the sheathing procedure resulting in a percentage of scrap from this process.

Most catheter manufacturing devices process multiple catheters per cycle by means of duplicate heating elements mounted on one moving carriage. Other known catheter manufacturing devices have also required the inclusion of an extender mandrill and heat shrink to prevent pre-heating of the catheter body and sheathing material as loaded in the $1^{st}$, $2^{nd}$, $3^{rd}$ and/or remaining 10 positions, prior to a heating cycle initiation.

Also, the air heated by the known heating elements has well over half of its heat energy not used for processing product. Known catheter manufacturing devices have electrical resistive heaters which are at least two times as long and at least twice the diameter of the envisioned device. Known catheter manufacturing devices resistive heaters capacity is needed to heat the stainless-steel tube which in turn heats the exchangeable inner copper alloy tube. This waste heat produced by the outer surfaces of the resistive heater, stainless steel tube and minimal amount from the top and bottom of the copper alloy tube is dissipated into the surrounding environment which leads to higher cooling costs for the controlled environments needed for the sterile manufacturing of the catheters.

In many known catheter manufacturing devices ambient or cool air enters the heating element proximate to a bottom, and the air is heated by the interior of the heating element. The heated air effectuates a heat transfer to the sheathing polymers and the catheter body. The lower portion of the heating element does not heat the ambient or cool air to desired temperature instantly, where a lower portion length of the heating element is not able to transfer sufficient energy to shrink the sheathing polymers to the catheter body nor transfer sufficient heat for fusion to the catheter body layers. Similarly some of the upper portion of the heating element cannot provide the required processing temperature for catheter formation.

In the known catheter manufacturing devices most air heated is dissipated into the surrounding environment as waste heat.

The art referred to and/or described above is not intended to constitute an admission that any patent, publication or other information referred to herein is "prior art" with respect to this invention. In addition, this section should not be construed to mean that a search has been made or that no other pertinent information as defined in 37 C.F.R. § 1.56(a) exists.

All U.S. patents and applications and all other published documents mentioned anywhere in this application are incorporated herein by reference in their entirety.

Without limiting the scope of the invention, a brief description of some of the claimed embodiments of the invention is set forth below. Additional details of the summarized embodiments of the invention and/or additional embodiments of the invention may be found in the Detailed Description of the Invention below.

A brief abstract of the technical disclosure in the specification is provided for the purposes of complying with 37 C.F.R. § 1.72.

GENERAL DESCRIPTION OF THE INVENTION

In one embodiment, the thermo-coupling component provides efficient conductive heat transfer to the heating element. The heating element then heats ambient gas/air as the gas/air moves upward through the central vertical passage of the heating element. The size of the central vertical passage permits the processing of a wide range of catheter diameters without the need to exchange heating components.

In some embodiments the Heater System and Device for Catheter Manufacturing provides a more consistent processing temperature over the length of the heating element allowing faster processing/shorter cycle times during catheter formation. In some alternative embodiments, a heating element having a shorter longitudinal dimension may be used to achieve the same energy transfer/heating during the manufacture of a catheter. The disclosed heating element minimizes the necessity for heating element replacement, by accommodating different diameter catheter bodies.

In some embodiments, the Heater System and Device for Catheter Manufacturing minimizes the waste of thermal energy, thereby reducing operational cost. Further in some embodiments, the Heater System and Device for Catheter Manufacturing reduces/eliminates the requirement for compressed clean air or compressed nitrogen gasses needed for catheter formation.

In a preferred embodiment, the Heater System and Device for Catheter Manufacturing includes a heating element formed of a unitary piece of copper alloy material which accommodates multiple size catheters during the manufacturing process during a single manufacturing cycle. The copper alloy for the heating element has a very high coefficient of heat transfer. The heating element includes an increased surface area established through the inclusion of an inner bore which may have surface area increasing geometries. The heating element maintains a processing temperature for a selected size, type or combination of sheathing polymers and catheter bodies.

In a preferred embodiment, the heating element for the Heater System and Device for Catheter Manufacturing includes a plurality of first gas flow passages, or first super charge gas flow passages, extending from the heating element outer diameter to the inner diameter of the central vertical passage. The first gas flow passages may be positioned and equally spaced around the circumference of the heating element. In some embodiments the first gas flow passages may be disposed at an angle with respect to the longitudinal axis or centerline of the central vertical passage. The first gas flow passages from the outer diameter of heating element to the inner diameter of central vertical passage may be located on the upper portion of the heating element and enter into the inner diameter of central vertical passage at a higher location as compared to the entry location on the outer diameter of heating element. The oblique angle for the first gas flow passages provide a increased heating distance and surface area to provide heat transfer to gases flowing through the first gas flow passages.

In at least one embodiment, establishment of a turbulent heated gas flow proximate to the sheathing and catheter body within the central vertical passage facilitates the even disposition of polymers onto the catheter. The first gas flow passages provide for the turbulent heated gas flow within the central vertical passage and proximate to the sheathing and catheter body components. Heated gas is not forced through the first gas flow passages but occurs naturally through a chimney like effect. Establishment of a turbulent gas flow within the central vertical passage improves the transfer of heat energy to the catheter body and sheathing material.

In at least one embodiment, a insulation chamber surrounds the heating element. The insulation chamber restricts heated gas dissipation which is proximate to the exterior of the thermo-coupling component and heating element. Gas at ambient temperature enters the insulation chamber through lower openings. The entering gas from the lower openings is then heated by the thermo-coupling component and the outer diameter of the heating element. The heated gas within the insulation chamber is heated further by passage through the first gas flow passages into the central vertical passage. The gas flow through the lower openings into the insulation chamber may also occur. The gas exit pathway is restricted through the top or upper portion of the inner diameter of central vertical passage, creating turbulence therein.

In at least one embodiment, the gas within the Heater System and Device for Catheter Manufacture encounters an iris/variable orifice which is sealed relative to the lower end of the central vertical passage. The iris/variable orifice may provide for passage of a fixed or variable volume of gas into the central vertical passage. Contact between the iris/variable orifice and the sheathing material for the catheter does not provide a hermitic seal and enables minimal ambient temperature gas flow directly into the bottom/lower end of the central vertical passage. A less restrictive parallel gas flow into the central vertical passage is provided through the first and second gas flow passages creating turbulence therein.

A minimal volume of gas at ambient temperature passes the iris/variable orifice directly into the central vertical passage. A larger volume of gas at ambient temperature passes through the lower openings into the insulation chamber and proximate to the exterior of the heating element, and then passes through the first and second gas flow passages and into the central vertical passage for heating.

In some embodiments the iris/variable orifice regulates or restricts the volume of gas entering into the central vertical passage for heating. The lower openings also restrict or regulate the volume of gas entering into the first and second gas flow passages and then into the central vertical passage, providing for more efficient heat transfer onto the polymer sheathing material during the catheter manufacturing process.

In some embodiments the iris/variable orifice also provides mechanical centering of the catheter in the central vertical passage. Non centered catheters passing through the central vertical passage cause the circumference of the catheter closest to the central vertical passage wall to receive more heat energy which distorts and creates non uniform walls about the circumference of the catheter.

The control of the volume of gas at ambient temperature into the insulation chamber, coupled with control of heated gas exposed to the increased surface area/heat transfer surfaces, increases the effective processing length of the heating element at a desired temperature.

In at least one embodiment, portions of the central vertical passage may include threads or other types of surface area increasing geometries to facilitate heat transfer and/or turbulence for the gas within the central vertical passage, and onto the sheathing material to constrict and conduct heat to the catheter body.

In some embodiments, the second gas flow passages, or second super charge gas flow passages, extend from the heating element outer diameter to the inner diameter of the central vertical passage. The second gas flow passages may be positioned and equally spaced around the circumference of the heating element. In some embodiments the second gas flow passages may be disposed at an angle with respect to a longitudinal axis or centerline of the central vertical passage. The second gas flow passages from the outer diameter of heating element to the inner diameter of central vertical passage may be located on a lower portion of the heating element, and enter into the inner diameter of central vertical passage at a higher location as compared to the entry location on the outer diameter of heating element. The oblique angle of the second gas flow passages provide a increased heating distance and surface area to provide heat transfer to gases flowing through the second gas flow passages.

In some embodiments, the first gas flow passages and the second gas flow passages may be perpendicular relative to the longitudinal axis or centerline. Alternatively, the first gas flow passages and the second gas flow passages may be at any desired angular orientation relative to the longitudinal axis or centerline. In addition, the first gas flow passages and the second gas flow passages are not required to extend in the same direction or have the same angular orientation relative to the longitudinal axis or centerline, and may be in opposite angular directions. Further, the first gas flow passages and the second gas flow passages may be formed into curved or spiral shaped passages.

Each individual first gas flow passage or second gas flow passage may be uniform or non-uniform in shape, taper or diameter, having for example a larger gas inflow orifice and a smaller gas outflow orifice, a smaller gas inflow orifice and a larger gas outflow orifice, a larger gas inflow orifice and a smaller gas outflow orifice and a non-uniform diameter passage interior or a smaller gas inflow orifice and a larger gas outflow orifice and a non-uniform diameter passage interior, an increasing or decreasing interior passage diameter, an increasing or decreasing interior passage diameter which is larger or smaller relative to either of the gas inflow orifice or gas outflow orifice. The first gas flow passages and the second gas flow passages may additionally alternate in shape between adjacent passages or be formed into sets of similarly shaped passages. Further, each individual first gas flow passages and second gas flow passages may include the same or different interior structural elements to provide surfaces to increase or decrease heat transfer.

The heating element may also include third, fourth or multiple sets of gas flow passages located at any desired position between the first gas flow passages and the second gas flow passages. In addition, the first gas flow passages and the second gas flow passages may include any combination(s) of elements, configurations and/or structure as mentioned herein.

In at least one embodiment, the iris/variable orifice is formed of a plurality of individual flexible non-marring material discs. The center portion of each of the sealing discs is in contact with the shrink-fit tube which is the outer most layer of the catheter. The iris/variable orifice restricts the inflow of ambient/unheated air into the central vertical passage.

In at least one embodiment, the Heater System and Device for Catheter Manufacture includes at least two gas pathways for heating the polymer sheathing onto the catheter body. In one pathway the iris/variable orifice allows a small amount of gas to pass between the central triangular ends and the polymer sheathing and into the central vertical passage. In another pathway, gas flows between the upper surface of a coupler and the lower surface of a bottom plate and through a plurality of lower openings and the wire guide opening into the insulation chamber. The heated gas in the insulation chamber then enters into the first gas flow passages and/or second gas flow passages, and then into the central vertical passage. In both pathways gas exits through the upper orifice of the central vertical passage.

The majority of gas starting at ambient temperature passes through the insulation chamber and the first gas flow passages and/or second gas flow passages. The larger volume of gas passing through the insulation chamber and then into the central vertical passage occurs as a result of the combined area of gas flow passages provided by the lower openings and the first gas flow passages and/or second gas flow passages, as compared to the minor gas passage through the iris/variable orifice. In at least one embodiment, the dimension selected for the central vertical passage and top outflow orifice will constitute the gas flow restrictor for the Heater System and Device for Catheter Manufacture.

In some embodiments, the central vertical passage may be straight or formed into a curved or spiral shaped passage. The inner diameter of central vertical passage may be uniform or non-uniform in shape, or have a tapered diameter interior between the bottom inflow orifice and the top outflow orifice, having for example a larger bottom gas inflow orifice and a smaller top gas outflow orifice, a smaller bottom gas inflow orifice and a larger top gas outflow orifice, a larger bottom gas inflow orifice and a smaller top gas outflow orifice and a non-uniform diameter passage interior or a smaller bottom gas inflow orifice and a larger top gas outflow orifice and a non-uniform diameter passage interior, an increasing or decreasing interior passage diameter, an increasing or decreasing interior passage diameter which is larger or smaller relative to either of the top gas inflow orifice or the bottom gas outflow orifice.

The central vertical passage and/or the first and/or second gas flow passages in any combination may include interior structural elements to provide surfaces to increase or decrease heat transfer. The surface modifications or elements may include machined threads, openings, passages, knurls, raised or lowered surfaces, three dimensional printed, extension tubes affixed or attached to the outer surface of the heating element as aligned with the first and/or second gas flow passages thereby extending the length dimensions for the first and/or second gas flow passages, or a downward facing conic copper alloy structure, affixed to and circumventing the outer surface of the heating element approximate to and above the first or second gas flow passages. The conic structure would be conductively heated by the heating element and would funnel air heated by the cone into the gas flow passages.

Different portions of the central vertical passage and/or the first and/or second gas flow passages may include different surface modifications dependent on the requirements or specifications of a particular application. In addition, the central vertical passage and/or the first and/or second gas flow passages may include any combination(s) of elements, configurations and/or structure as mentioned herein.

In some embodiments, the heating element may have an outer diameter dimension of between ¾ inch and 1 inch. In other embodiments the heating element may have an outer diameter dimension less than ¾ inch or larger than 1 inch. In some embodiments, the heating element may have a length dimension of between 3 inches and 4 inches. In other embodiments, the heating element may have a length dimension less than 3 inches or longer than 4 inches.

In some embodiments, the heating element 14 may be comprised of multiple cylindrical segments stacked along its length. These segments may facilitate ease of manufacturing desired geometries in the central vertical passage 18 and/or the first and/or second gas flow passages 28, 38. These segments may be fastened to one another by silver soldering, laser welding or suitable mechanical fasteners.

In some embodiments, the heating element 14 may be comprised of multiple vertical cuts from the exterior to the central vertical passage 18 to form a two-piece clam shell arrangement or multiple pie shaped segments as viewed from the top of the heating element 14. These segments may facilitate ease of manufacturing desired geometries in the central vertical passage 18 and/or the first and/or second gas flow passages 28, 38. These segments may be fastened to one another by silver soldering, suitable mechanical fasteners, or held in place by the thermo-coupling component.

In some embodiments, the heating element 14 may be comprised of a non-cylindrical copper alloy block which when viewed from above could be a square, rectangle, or other suitable geometries. One or more central vertical passage 18 may be place through the entire height of a desired block shape. Replacing the cylindrical band heater style thermo-coupling element 12 with commonly available small elongated cylinder/"firerod" heaters placed in drilled holes parallel and approximate to the central vertical passage 18 in the block. This block arrangement allows for much longer first and/or second gas flow style passages 28, 38. Insulation geometries would contain the waste heat to be used to capture and reuse the waste heat as described herein.

In some embodiments the dimensions for the heating element have an impact on processing catheter manufacturing speeds, where smaller dimensions reduce processing speeds. However, uniformity of temperature over an entire processing length may be of higher importance for quality control standards as compared to processing speeds.

In at least one embodiment, the iris/variable orifice may include an adjustable feature. In some embodiments an iris/variable orifice may be located at both the top and the bottom of the Heater System and Device for Catheter Manufacture.

In some embodiments an iris/variable orifice 36 may be located above the top plate and not placed to control air flow but strictly serve as the beneficial centering mechanism of the catheter in the central vertical passage.

A heating assembly for a catheter manufacture machine, said heating assembly includes an elongate heating element having an outer diameter, a central vertical passage, an upper end and a lower end, said heating element having a longitudinal axis, said central vertical passage extending in the direction of said longitudinal axis, said central vertical passage being centrally disposed relative to said heating element traversing said upper end and said lower end; and a plurality of first gas flow passages traversing said heating element, said first gas flow passages extending from said outer diameter at an angle relative to said longitudinal axis traversing an inner diameter of said central vertical passage proximate to said upper end, wherein said first gas flow passages traversing said outer diameter are constructed and arranged as a gas inlet, and said first gas flow passages traversing said inner diameter of the central vertical passage, which are constructed and arranged as a gas outlet into said central vertical passage, said first gas flow passages traversing said outer diameter of heating element at a first distance from said upper end which is larger than a second distance between said first gas flow passages traversing said inner diameter and said upper end, said first gas flow passages being further constructed and arranged for passage of previously heated gas exterior to said heating element into said central vertical passage.

While the foregoing is a brief description of some of the embodiments for carrying out the invention for the purposes of complying with 37 C.F.R. 1.72., it is also intended in an illustrative rather than a restrictive sense. Variations to the exact embodiments described may be apparent to those skilled in such equipment without departing from the spirit and scope of the invention as defined by the claims set out below.

These and other embodiments which characterize the invention are pointed out with particularity in the claims annexed hereto and forming a part hereof. However, for further understanding of the invention, its advantages and objectives obtained by its use, reference should be made to the drawings which form a further part hereof and the accompanying descriptive matter, in which there is illustrated and described embodiments of the invention.

9

Figure 1:
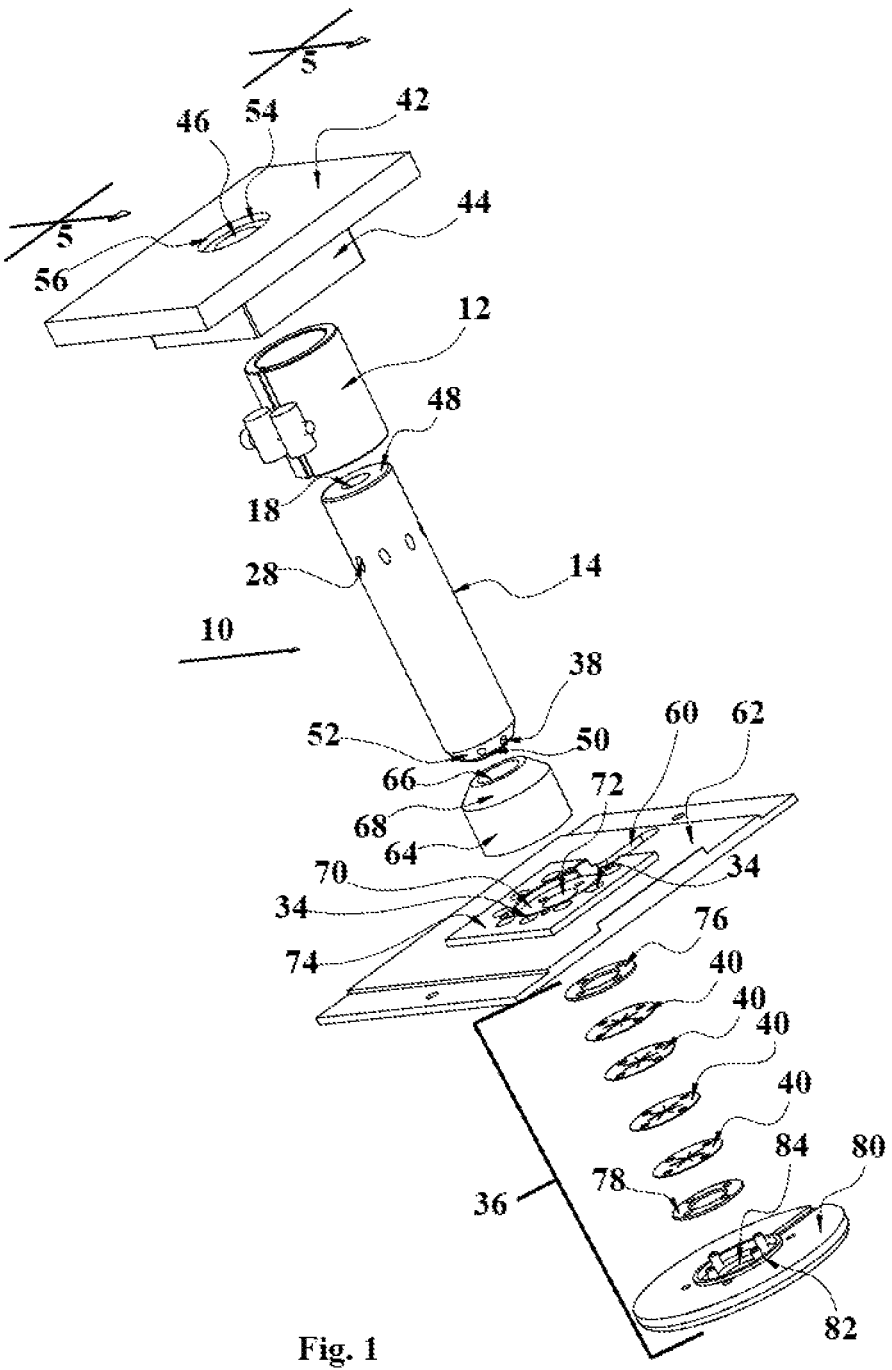
FIG. 1 is a partial front exploded isometric perspective view of one alternative embodiment of the Heater System and Device for Catheter Manufacture.

DETAILED DESCRIPTION OF THE
PREFERRED EMBODIMENTS

In general, the Heater System and Device for Catheter Manufacture is identified by reference numeral 10.

Referring to FIG. 1 through FIG. 7, in at least one embodiment the Heater System and Device for Catheter Manufacture 10 includes a top plate 42. The top plate 42 has a lower surface having an interface structure 44. The top plate 42 may be formed of metallic material and in some embodiments may not be insulated. In other embodiments the top plate 42 may be formed or coated with insulative material. The interface structure 44 may be formed of metallic material and in some embodiments may not be insulated. In other embodiments the interface structure 44 may be formed or coated with insulative material forming a cover for the insulation chamber 32.

In at least one embodiment, the top plate 42 includes a centrally positioned top plate gas outflow opening 46. The top plate gas outflow opening 46 traverses the top plate 42 and the interface structure 44 and is in gas flow communication with the upper end 48 of central vertical passage 18. The top plate gas outflow opening 46 is the location for heated gas originating in the insulation chamber 32, central vertical passage 18, first gas flow passages 28 and second gas flow passages 38 to exit.

In some embodiments the top plate 42 and interface structure 44 may be rectangular, square, circular or oval in shape dependent upon the requirements of a particular application.

In at least one embodiment, the upper surface of top plate gas outflow opening 46 may include a circular recess 54. The circular recess 54 is preferably sized to receive a second iris/variable orifice 36. A second iris/variable orifice 36 may be placed into the circular recess 54 to surround a catheter body 88 and sheathing material 90 following heat transfer, and to further restrict gas exit from the interior of insulation chamber 32, central vertical passage 18, first gas flow passages 28 and second gas flow passages 38. Use of a second iris/variable orifice 36 may also assist in the positioning and alignment of the catheter body 88 and sheathing material 90 centrally relative to the interior of the central vertical passage 18 post heat transfer. The inclusion of a second iris/variable orifice 36 improves the reliability and performance of the manufacturing process, and resulting a higher quality of catheter product.

In a preferred embodiment, the top plate gas outflow opening 46 is preferably the same size as the diameter dimension for the central vertical passage 18. The underside of the interface structure 44 includes a centrally positioned circular receiving guide 56. The receiving guide is sized to receive the outer diameter of heating element 16 and locate the heating element 14 in a stationary position relative to the top plate 42, and the interface structure 44, during manufacture of the catheter. Fixed positioning of the heating element 14 relative to the interface structure 44 and top plate 42 improves the consistency and quality of manufactured catheters while simultaneously reducing undesired waste heat gas outflow.

In some embodiments, the upper end 48 is preferably engaged to a ledge on the underside of the top plate 42 as established by the receiving guide 56. The positioning of the upper end 48 within the receiving guide 56 also restricts gas flow passage within the insulation chamber 32, requiring gas flow passage through the central vertical passage 18, first gas flow passages 28 and second gas flow passages 38, where the gas flow passage is exposed to a regulated amount of heat transfer.

The insulation chamber 32 is constructed and arranged to permit gas at ambient temperature to enter into the insulation chamber 32, but to restrict the escape of heated gas from the interior of the insulation chamber 32. The intent of the insulation chamber 32, central vertical passage 18, first gas flow passages 28 and second gas flow passages 38 is to use otherwise wasted outside surface heating energy of the thermo-coupling component 12 and heating element 14, to significantly increase the gas temperature above ambient temperature prior to entering the central vertical passage 18, first gas flow passages 28 and second gas flow passages 38. The insulation chamber 32 is a reservoir of heated air that requires less heating by the first gas flow passages 28, second gas flow passages 38 and central vertical passage 18 to reach the desired product processing temperature.

In at least one embodiment, the gas flow passage within the insulation chamber 32 through the first gas flow passages 28 and second gas flow passages 38 into the central vertical passage 18, in conjunction with the exposure of the gas to a regulated amount of heat, creates gas turbulence within the central vertical passage 18. The heated gas turbulence facilitates the manufacturing process for the catheter 22 by the provision of an even exposure of heat transfer from heated gas onto the sheathing material 90 and to the catheter body 88, at all locations within the central vertical passage 18, including areas immediately proximate to the upper end 48 and the lower end 50.

The Heater System and Device for Catheter Manufacture 10 minimizes the exposure of gas having an ambient temperature proximate to and within the central vertical passage 18, and minimizes the existence of temperature differentials proximate to the upper end 48 and lower end 50.

In some embodiments, heated gas turbulence within the central vertical passage 18 facilitates the manufacturing process for the catheter 22 by providing an even distribution of the turbulent gas within the central vertical passage 18. The centering of the sheathing material and the catheter body 88 within the central vertical passage 18, in turn, enables a single heating element 14 to be used in the manufacture of multiple diameters of catheter 22, eliminating the necessity for substitution or replacement of heating elements 14 dependent on a desired diameter size of catheter product.

Figure 2:
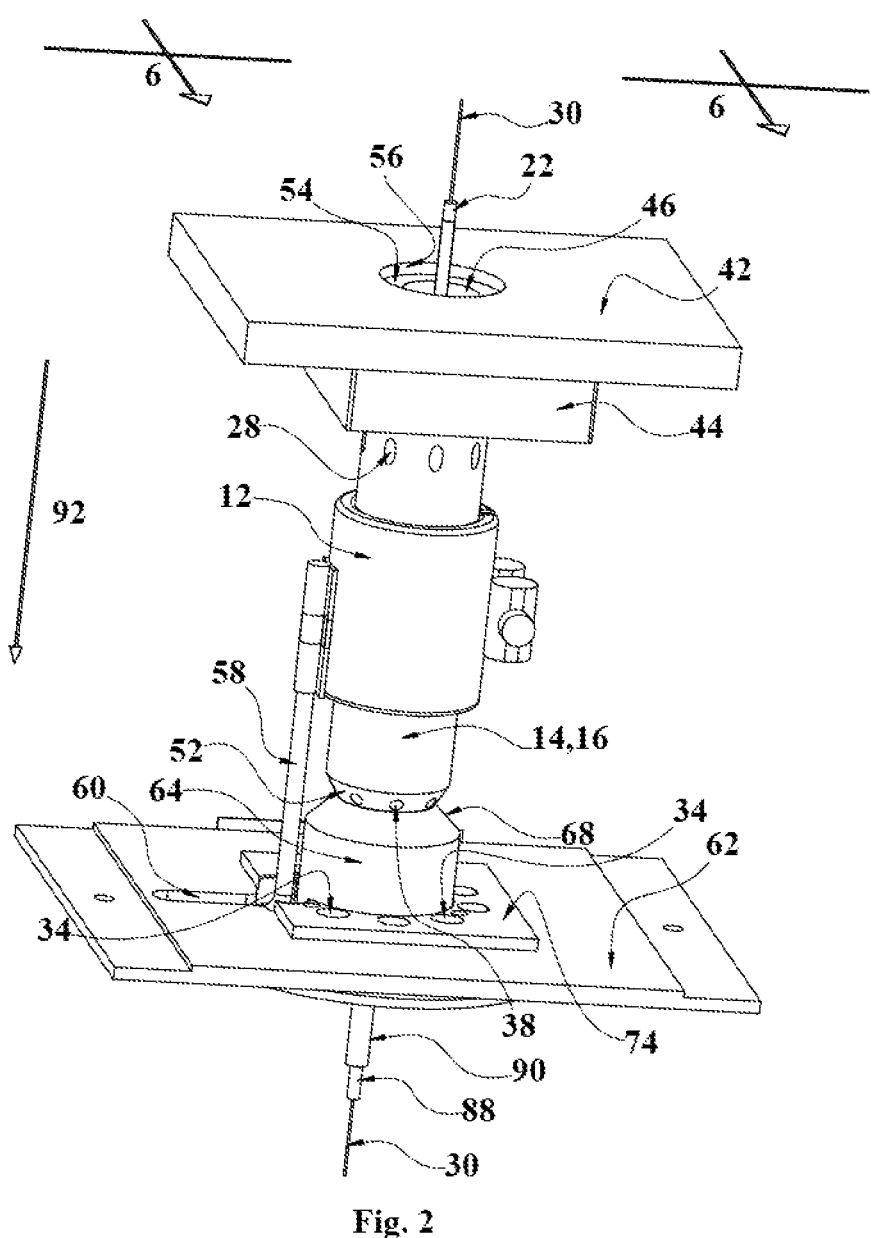
FIG. 2 is a partial back elevation view of one alternative configuration of the Heater System and Device for Catheter Manufacture.

The heating element 14 is substantially cylindrical in shape and includes the central vertical passage 18 which is centrally located within the interior. The central vertical passage 18 extends vertically through the interior of the heating element 14 and establishes a gas outflow opening proximate to the upper end 48. The lower end 50 of the heating element 14 may include a chamfer edge 52. In at least one embodiment the central vertical passage 18 includes a vertical longitudinal axis or centerline 30 as shown in FIG. 2.

In a preferred embodiment, the inflow orifices for the plurality of second gas flow passages 38 are located, and equally spaced relative to each other, on the chamfer edge 52. The outflow orifices for the plurality of second gas flow passages 38 traverse the inner diameter of central vertical passage 20, establishing gas flow passages through the lower portion of the heating element 14, into the interior of the central vertical passage 18. When the heating element 14 is heated, the second gas flow passages 38 function to provide additional heat transfer to gas passing from the interior of the insulation chamber 32 into the central vertical passage 18. The central vertical passage 18 is in surrounding engagement of a catheter body 88 and sheathing material 90, where the sheathing material 90 is in intimate contact and is compressing and heating the catheter body 88 upon exposure to heated gas, during the passing of the catheter 22 vertically upward from the lower end 50 toward the upper end 48, during the manufacture of the catheter 22.

In at least one embodiment the sheathing material 90 and the catheter body 88 is held stationary from above and the Heater System and Device for Catheter Manufacture 10 is initially located in a top or elevated position. During the manufacturing process the Heater System and Device for Catheter Manufacture 10 is lowered along the sheathing material 90 and the catheter body 88, where the formed catheter 22 following heating exits the top plate gas outflow opening 46. In at least one alternative embodiment, the direction of movement of the Heater System and Device for Catheter Manufacture 10 may be reversed, for elevation relative to the sheathing material 90 and the catheter body 88, where the formed catheter 22 exits the bottom plate catheter orifice 72.

In a preferred embodiment, the inflow orifices for the plurality of first gas flow passages 28 are located, and equally spaced relative to each other, proximate to the upper end 48. The outflow orifices for the plurality of first gas flow passages 28 traverse the inner diameter of central vertical passage 20, establishing gas flow passages through the upper portion of the heating element 14 into the interior of the central vertical passage 18. When the heating element 14 is activated, the first gas flow passages 28 function to provide additional surface area for heat transfer to gas passing from the interior of the insulation chamber 32 into the central vertical passage 18. In alternative embodiments, the first gas flow passages 28 may be located at any desired position relative to the heating element 14, between the upper end 48 and the lower end 50. In addition, the first gas flow passages 28 are not required to be horizontally aligned relative to each other and may be offset vertically relative to an adjacent first gas flow passages 28, may form a spiral or regular descending or ascending configuration, may form an angular descending or ascending configuration, may form a sinusoidal or undulating configuration, or may form an alternating configuration, or may form any combination of configurations, to name a few of the multitude of examples of configurations or patterns for the first gas flow passages 28 on the heating element 14.

In at least one embodiment, a thermo-coupling component 12 may be a resistive element heater or a band heater which is in surrounding engagement to a portion of the exterior of the heating element 14. The thermo-coupling component 12 is electrically connected to a power source to provide conduction energy transfer to the heating element 14, and to heat the heating element 14 for processing of the sheathing material 90 and catheter body 88 moving through the central vertical passage 18. An electrical connection wire 58 may be releasably coupled to the thermo-coupling component 12, and the wire 58 may pass through a wire guide 60 traversing a bottom plate 62. Ambient temperature gas may also pass through an unobstructed portion of the wire guide 60 into the insulation chamber 32.

In at least one embodiment, an insulated platform 64 is disposed below the lower end 50 and above the bottom plate 62. The platform 64 may be substantially cylindrical in shape and may include a partial conical shaped upper section. The apogee of the platform 64 includes a catheter passage opening 66 which permits the sheathing material 90 and catheter body 88 to pass upwardly from the bottom plate 62 and the platform 64 during the manufacturing process.

The catheter passage opening 66 is aligned with, and is preferably the same dimension as the central vertical passage 18. The contact between the apogee of the platform 64 with the lower end 50 restricts gas passage into the insulation chamber 32, the first gas flow passages 28 or the second gas flow passages 38. The apogee of the platform 64 may also include a second chamfered edge 68 which is in an opposite direction relative to the chamfer edge 52. The opposite relative directions between the chamfer edge 52 and the second chamfered edge 68 provide additional space for gas flow passage into the second gas flow passages 38.

In some embodiments, the bottom plate 62 includes a bottom plate elevated portion 74 having a circular bottom plate recessed area 70 and a centrally positioned and circular shaped bottom plate catheter orifice 72. A plurality of lower openings 34 traverse the bottom plate 62, and bottom plate elevated portion 74, providing for a gas flow passage into the interior of the insulation chamber 32.

In at least one embodiment the bottom plate recessed area 70 is sized to receive the bottom and lower portion of the platform 64 to prevent gas flow passage between the bottom plate elevated portion 74 and the platform 64.

Any number, size or geometries of lower openings 34 may be traversing the bottom plate 62 and the bottom plate elevated portion 74, proximate the perimeter of the bottom plate recessed area 70 to permit gas inflow into the interior of the insulation chamber 32. The number of lower openings 34 selected for inclusion through the bottom plate 62 will vary dependent on a particular application. It is anticipated that at least three lower openings 34 will be utilized. It is also anticipated that less than ten lower openings 34 will be utilized to provide gas flow inlet passages. However, it should be noted that less than three or more than ten lower openings 34 may be used in particular applications, and the number of lower openings 34 identified herein have been provided without restriction for illustrative purposes.

In a preferred embodiment an iris/variable orifice 36 is disposed below the bottom plate 62 and is positioned in a receiving recess 86. The center of the iris/variable orifice 36 is vertically aligned with the center of the bottom plate catheter orifice 72. The iris/variable orifice 36 may include an upper washer 76, a plurality of sealing discs 40 below the upper washer 76, a lower washer 78 immediately below the plurality of sealing discs 40, and a coupler 80 having an elevated portion 82 and a centrally positioned and circular shaped coupler orifice 84. The elevated portion 82 functions as a base or platform for engagement to the lower washer 78. The coupler 80 is preferably used to compress the lower washer 78, the sealing discs 40 and upper washer 76 upwardly against the lower surface of the bottom plate 62. The catheter body 88 and sheathing 90 will pass upwardly through the center of the coupler orifice 84, lower washer 78, sealing discs 40, upper washer 76 and bottom plate catheter orifice 72, for receipt of heat transfer to the sheathing material 90 within the heating element 14.

Figure 6:
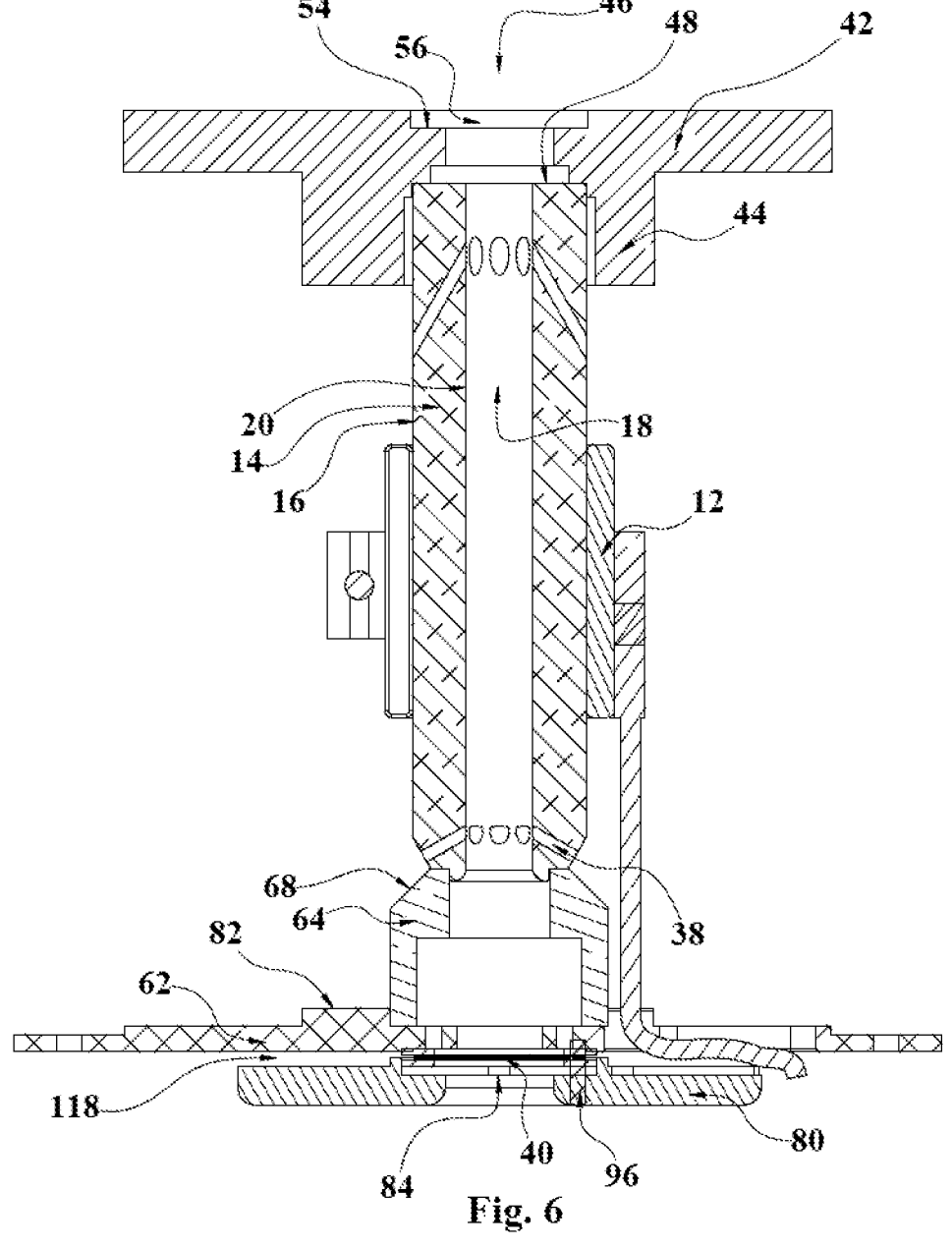
FIG. 6 is a partial cross-sectional side view of one alternative embodiment of the Heater System and Device for Catheter Manufacture taken along the line 6-6 of FIG. 2.
Figure 7:
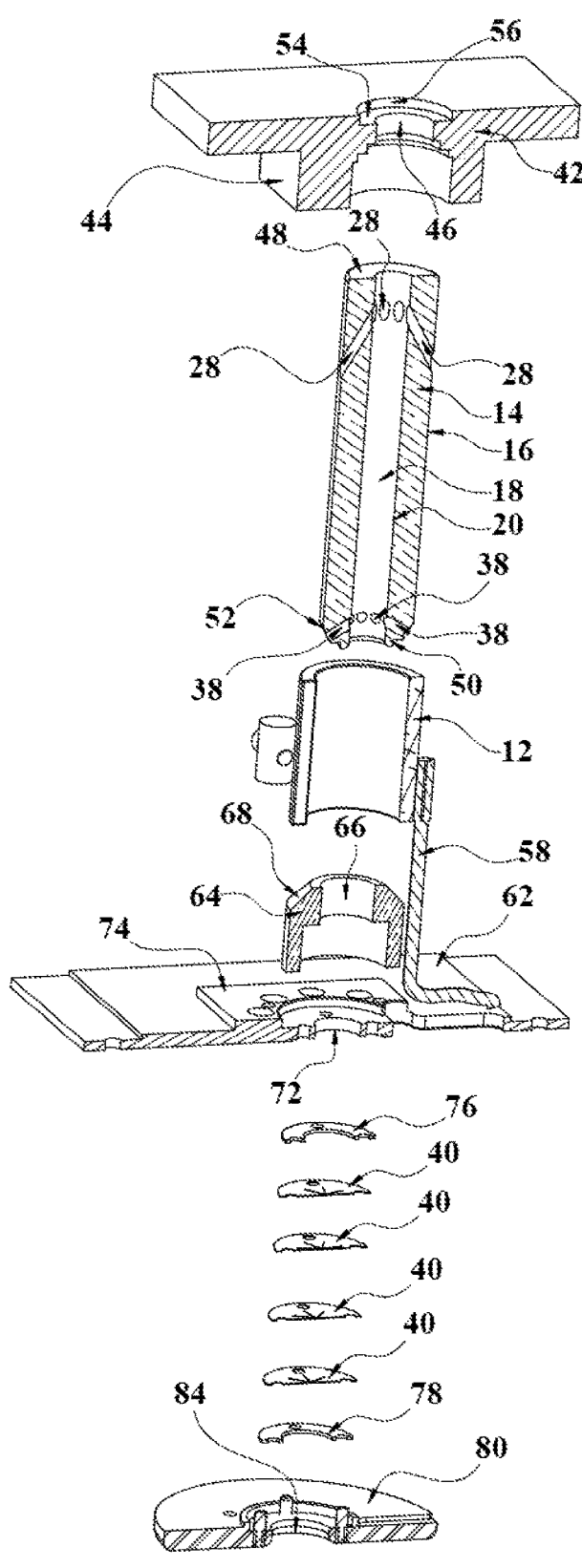
FIG. 7 is a partial cross-sectional side view of one alternative embodiment of the Heater System and Device for Catheter Manufacture taken along the line 7-7 of FIG. 4.
Figure 13:
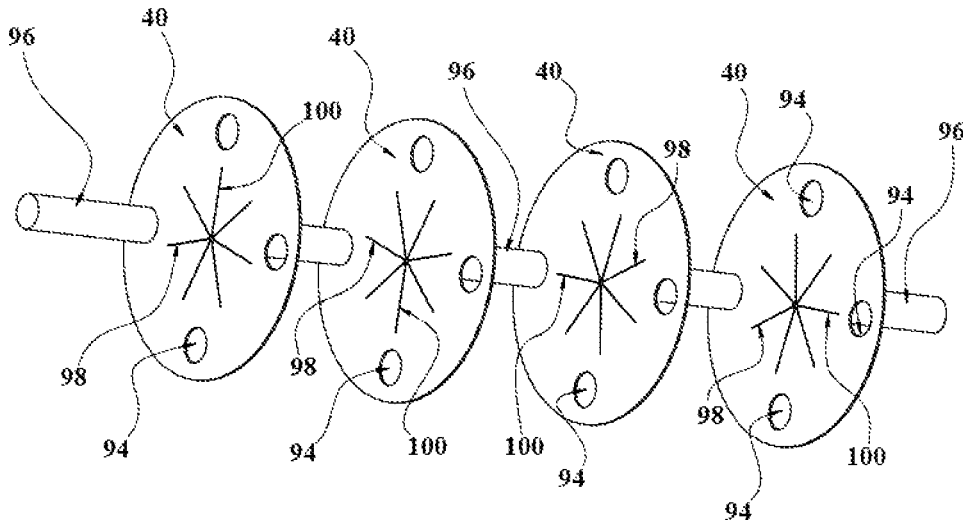
FIG. 13 is a detail front exploded perspective view of one alternative embodiment of the iris/variable orifice.

In at least one embodiment, as may be seen in FIG. 6 and FIG. 13 a plurality of disc positioning/fastening elements 96 may be press fit/attached to the coupler 80, lower washer 78, sealing discs 40, upper washer 76 and bottom plate 62. The plurality of disc positioning/fastening elements 96 pass through the disc positioning apertures 94 of the sealing discs 40. The plurality of disc positioning/fastening elements 96 control the rotational position of the coupler 80, lower washer 78, sealing discs 40, and the upper washer 76 relative to the bottom plate 62. The plurality of disc positioning/ fastening elements 96 place the lower washer 78, sealing discs 40, and the upper washer 76 in a fixed orientation relative to the coupler 80 and the bottom plate 62. The plurality of disc positioning/fastening elements 96 also function to retain the coupler 80 in a compacted operative position relative to the bottom plate 62.

In at least one embodiment, the plurality of disc positioning/fastening elements 96 may be dowel rods, dowel pins, pins, screws, bolts, pegs, or any other type of mechanical fastener member as required for a particular application.

Figure 3:
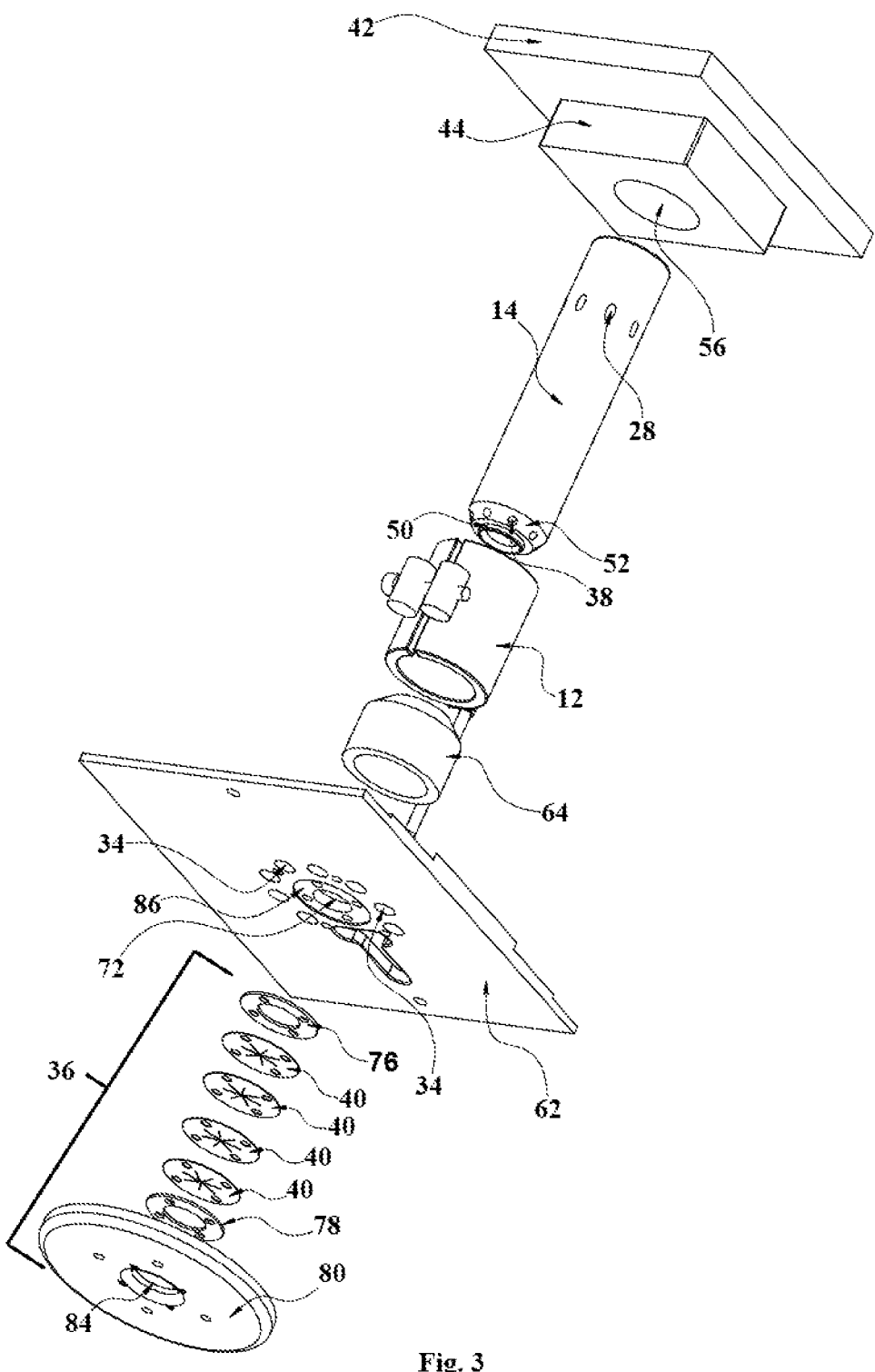
FIG. 3 is a partial alternative front exploded isometric perspective view of one alternative embodiment of the Heater System and Device for Catheter Manufacture.
Figure 4:
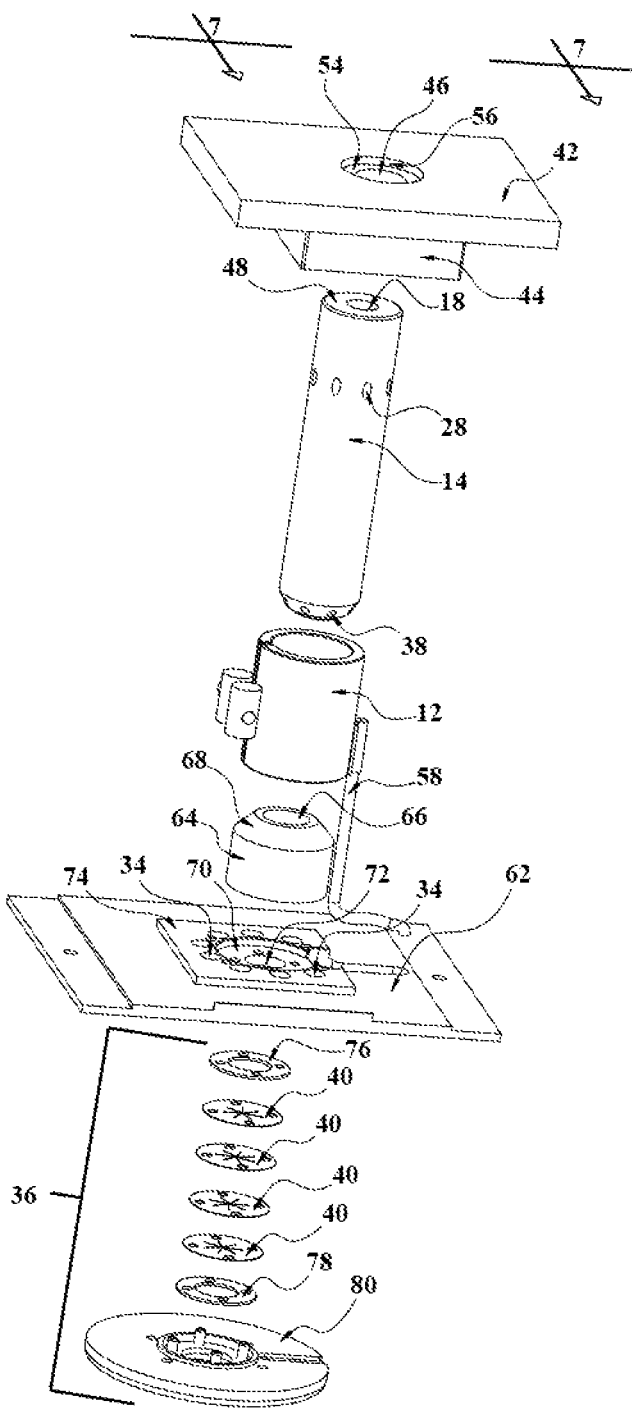
FIG. 4 is a partial alternative front exploded isometric perspective view of one alternative embodiment of the Heater System and Device for Catheter Manufacture.
Figure 5:
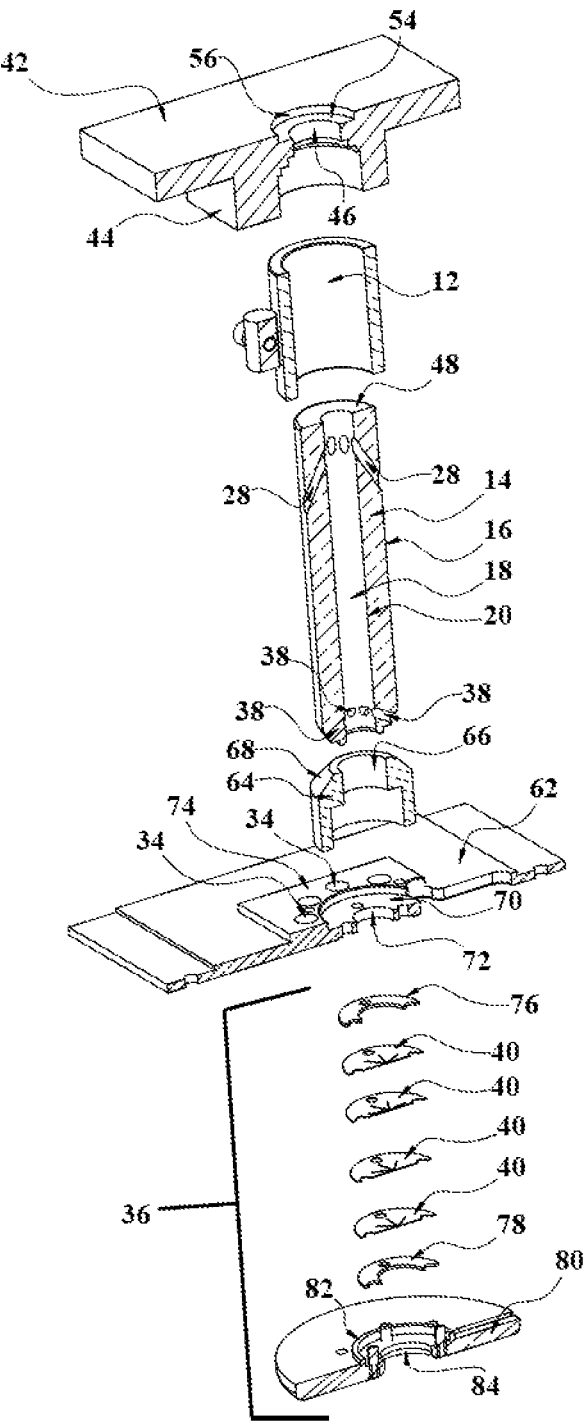
FIG. 5 is an isometric partial cross-sectional side view of one alternative embodiment of the Heater System and Device for Catheter Manufacture taken along the line 5—of FIG. 1.

In addition to the elements as previously identified in FIG. 1 and FIG. 2, FIG. 3 shows the lower surface of the bottom plate 62. The lower surface of bottom plate 62 includes a centrally positioned and circular shaped receiving recess 86 which is preferably sized, and is constructed and arranged to receive and position the upper washer 76 or the sealing discs 40, for alignment with the catheter passage opening 66 of the platform 64, and the central vertical passage 18 of the heating element 14.

In at least one embodiment, as shown in FIG. 6, in an assembled position, a gap is present between the lower surface of the bottom plate 62 and the upper surface of the coupler 80. The gap between the lower surface of the bottom plate 62 and the upper surface of the coupler 80 provides an ambient temperature gas passage represented by arrow 118, permitting gas passage between the bottom plate 62 and the coupler 80, through the lower openings 34 in the bottom plate 62, and into the insulation chamber 32. The gas in the insulation chamber 32 will enter into the first gas flow passages 28 or the second gas flow passages 38 and then into the central vertical passage 18.

A very minimal volume of gas at ambient temperature will vertically pass the bottom plate 62 through the iris/variable orifice 36 and into the central vertical passage 18. The primary passage of gas at ambient temperature will vertically pass the bottom plate 62 through the ambient temperature gas passage 118, the lower openings 34 and into the insulation chamber 32, as well as the passage of gas at ambient temperature through the wire guide 60 and into insulation chamber 32.

In at least one embodiment the bottom plate 62 is not insulated. However, the bottom plate 62 may be insulated as required by a particular application.

Figures 8, 9, 10, 11, 12:
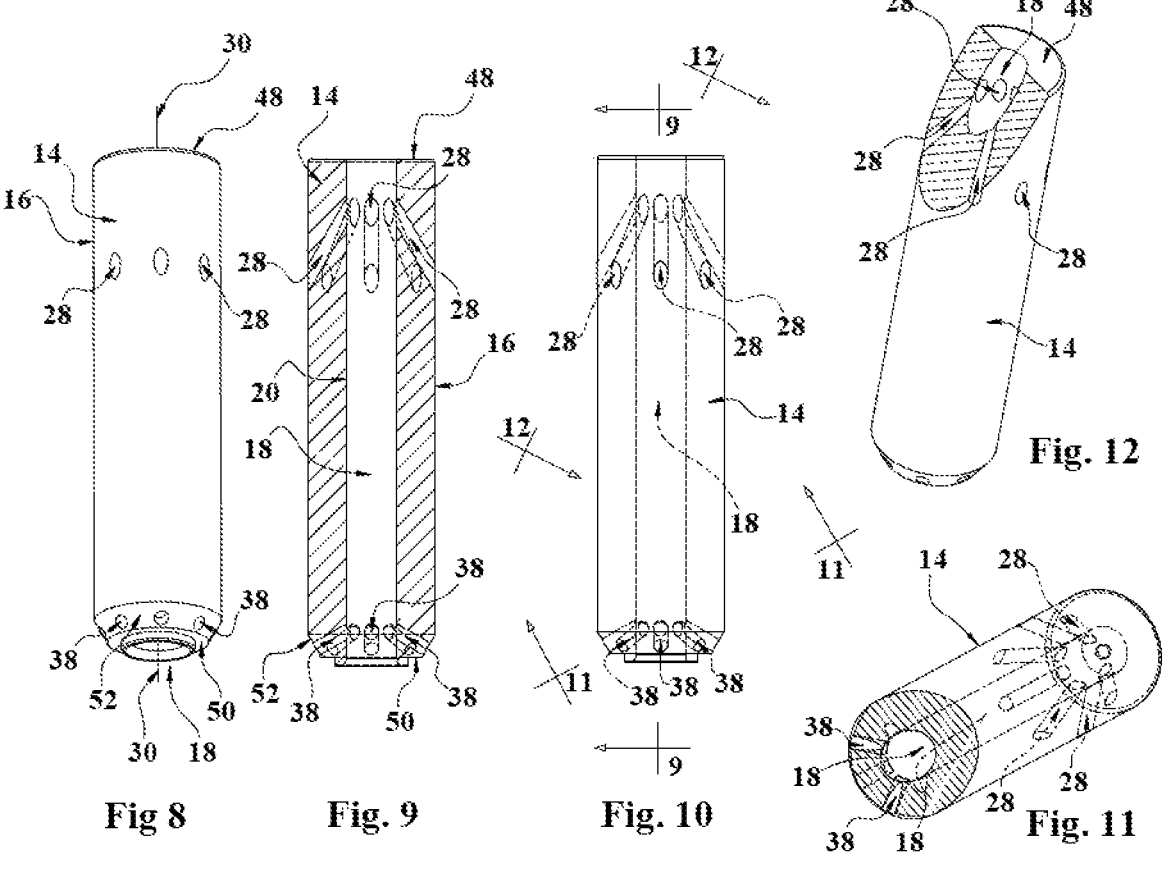
FIG. 8 is a detail front isometric perspective view of one alternative embodiment of the heating element.
FIG. 9 is a cross-sectional side view of one alternative embodiment of the heating element taken along the line 9-9 of FIG. 10.
FIG. 10 is a detail front elevation view of one alternative embodiment of the heating element showing the first and second gas flow passages in phantom line.
FIG. 11 is a detail perspective cross-sectional bottom view of one alternative embodiment of the heating element taken along the line 11-11 of FIG. 10, further showing the first gas flow passages in phantom line.
FIG. 12 is a detail perspective cross-sectional top view of one alternative embodiment of the heating element taken along the line 12-12 of FIG. 10.

In at least one preferred embodiment, a heating element 14 is depicted in FIG. 8 through FIG. 12. FIG. 8 shows the exterior of the heating element 14 including the first gas flow passages 28 and the second gas flow passages 38 and the longitudinal axis or centerline 30 extending vertically through the center of the central vertical passage 18.

As may be seen in FIG. 8 through FIG. 12, the first gas flow passages 28 are located proximate to the upper portion of the heating element 14. The first gas flow passages 28 traverse the outer diameter of heating element 16 from the exterior of the heating element 14, extending inwardly and passing through the inner diameter of central vertical passage 20, providing gas flow communication with the central vertical passage 18.

In some embodiments, the first gas flow passages 28 may be positioned and equally spaced around the circumference of the heating element 14. The first gas flow passages 28 are preferably disposed at an angle with respect to the longitudinal axis or centerline 30 of the central vertical passage 18. In general, the first gas flow passages 28 traverse the outer diameter of heating element 16 at a lower position on the heating element 14 relative to the passing of the first gas flow passages 28 through the inner diameter of central vertical passage 20 and into the central vertical passage 18, which occurs at a higher position on the heating element 14. The angular orientation of the first gas flow passages 28 relative to the longitudinal axis or centerline of the heating element 14 and central vertical passage 18, increase the surface area of the first gas flow passages 28, improving heat transfer onto the gas flowing through the first gas flow passages 28 for exposure to the sheathing material 90 and catheter body 88 within the central vertical passage 18.

In some embodiments, when a smaller surface area for heat exchange from the heating element 14 to the gas is desired, the first gas flow passages 28 may be perpendicular relative to the longitudinal axis or centerline 30. Alternatively, the first gas flow passages 28 may be at any desired angular orientation relative to the longitudinal axis or centerline 30.

A smaller acute angle between the first gas flow passages 28 and the longitudinal axis or centerline 30 will provide less heat transfer surface area from the heating element 14 for heating of gas within the insulation chamber 32 for exposure to the sheathing material 90 and catheter body 88. A larger acute angle between the first gas flow passages 28 and the longitudinal axis or centerline 30 will provide more heat transfer surface area from the heating element 14, for heating of gas within the insulation chamber 32 for exposure to the sheathing material 90 and catheter body 88. An acute angle between the first gas flow passages 28 and the longitudinal axis or centerline 30 is anticipated to be equal to or exceeding 15 degrees, and equal to or less than 75 degrees. The acute angle may be identified by visualization of an imaginary line extending perpendicular to the outer diameter of heating element 16 which passes through the center of the opening of the first gas flow passages 28, and the visualization of a second imaginary line extending angularly upward from the perpendicular line, the second line being centered within the first gas flow passages 28 and traversing the inner diameter of central vertical passage 20 into the central vertical passage 18. The acute angle will be the angle between the perpendicular line and the second line representing the first gas flow passages 28 through the inner diameter of central vertical passage 20 into the central vertical passage 18.

In an alternative embodiment, the first gas flow passages 28 and/or second gas flow passages 38 are not required to be in a two-dimensional plane relative to the central vertical passage 18 or longitudinal axis or centerline 30. The first gas flow passages 28 and/or second gas flow passages 38 may have a three dimensional direction or configuration relative to the longitudinal axis or centerline 30 extending in an upward and forward offset direction, or an upward and rearward offset direction in a "Z" plane. Further, the first gas flow passages 28 and/or second gas flow passages 38 may be formed into a curved or spiral shaped passage. The first gas flow passages 28 and/or second gas flow passages 38 may be the same shape, same angle, and/or have the same configuration as an adjacent first gas flow passages 28 and/or second gas flow passages 38.

Each individual first gas flow passages 28 and/or second gas flow passages 38 may be uniform or non-uniform in shape, taper or have a non-constant diameter. Each first gas flow passages 28 and/or second gas flow passages 38 may have for example a larger gas inflow orifice and a smaller gas outflow orifice; a smaller gas inflow orifice and a larger gas outflow orifice; a larger gas inflow orifice and a smaller gas outflow orifice and a non-uniform diameter passage interior; a smaller gas inflow orifice and a larger gas outflow orifice and a non-uniform diameter passage interior; an increasing and/or decreasing interior passage diameter which is larger or smaller relative to either of the gas inflow orifice or gas outflow orifice; a decreasing and then increasing interior passage diameter which is larger or smaller relative to either of the gas inflow orifice or gas outflow orifice; a decreasing and then increasing and then decreasing interior passage diameter which is larger or smaller relative to either of the gas inflow orifice or gas outflow orifice; an increasing and then decreasing and then increasing interior passage diameter which is larger or smaller relative to either of the gas inflow orifice or gas outflow orifice; a plurality of either decreasing or increasing interior passage diameters in any order, which is larger or smaller relative to either of the gas inflow orifice or gas outflow orifice; or the first gas flow passages 28 and/or second gas flow passages 38 may include any combination(s) of elements, configurations and/or structure as mentioned herein.

The first gas flow passages 28 and/or second gas flow passages 38 may include extension tubes attached to the outer diameter of the heating element 16. The inner diameter of the extension tubes preferably mimic the inside diameter of first gas flow passages 28 and/or second gas flow passages 38. The outside diameter and length of any extension tubes may vary as required in a particular application. In an alternative embodiment, A heating skirt encompassing the outer diameter of the heating element 16 may be adjacent to, and above the first gas flow passages 28 and/or second gas flow passages 38. The extension tubes and/or heating skirt provide additional structure and increase the heating surface area for the heating element 14.

The first gas flow passages 28 and/or second gas flow passages 38 may additionally alternate in shape between adjacent passages or be formed into sets of similarly shaped passages. Further, each individual first gas flow passages 28 and/or second gas flow passages 38 may include the same or different surface area increasing geometries 26 to provide surfaces to increase or decrease heat transfer to gas. The heating element 14 may also include third, fourth or multiple sets of gas flow passages located at any desired position between the first gas flow passages 28 and the second gas flow passages 38. In addition, the first gas flow passages 28 and/or second gas flow passages 38 may include any combination(s) of elements, configurations and/or structure as mentioned herein.

In some embodiments, the second gas flow passages 38 may be positioned and equally spaced around the circumference of the heating element 14. The second gas flow passages 38 are preferably disposed at an angle with respect to the longitudinal axis or centerline of the central vertical passage 18. In general, the second gas flow passages 38 traverse the outer diameter of heating element 16 at a lower position on the heating element 14 relative to the passing of the second gas flow passages 38 through the inner diameter of central vertical passage and into the central vertical passage 18, which occurs at a higher position on the heating element 14. The angular orientation of the second gas flow passages 38 relative to the longitudinal axis or centerline 30 of the heating element 14 and central vertical passage 18, increases the surface area of the second gas flow passages 38, improving heat transfer onto the gas flowing through the second gas flow passages 38 for exposure to the sheathing material 90 and catheter body 88 within the central vertical passage 18. It should be noted that the angular orientation for the second gas flow passages 38 relative to the longitudinal axis or centerline 30 is generally smaller than the angular orientation between the first gas flow passages 28 and the longitudinal axis or centerline 30.

In some embodiments, when a smaller surface area for heat exchange from the heating element 14 to the gas is desired, the second gas flow passages 38 may be omitted or the second gas flow passages 38 may be perpendicular relative to the longitudinal axis or centerline 30. Alternatively, the second gas flow passages 38 may be at any desired angular orientation relative to the longitudinal axis or centerline 30. A smaller acute angle between the second gas flow passages 38 and the longitudinal axis or centerline 30 will provide less heat transfer surface area from the heating element 14 for heating of gas within the insulation chamber 32 for exposure to the sheathing material 90 and catheter body 88. Alternatively a larger acute angle between the second gas flow passages 38 and the longitudinal axis or centerline 30 will provide more heat transfer surface area from the heating element 14, for heating of gas within the insulation chamber 32 for exposure to the sheathing material 90 and catheter body 88. An acute angle between the second gas flow passages 38 and the longitudinal axis or centerline 30 is anticipated to be equal to or exceeding 5 degrees, and equal to or less than 45 degrees. The acute angle may be identified by visualization of an imaginary line extending perpendicular to the outer diameter of heating element 16 which passes through the center of the opening of the second gas flow passages 38, and the visualization of a second imaginary line extending angularly upward from the perpendicular line, the second line being centered within second gas flow passages 38 and traversing the inner diameter of central vertical passage 20 into the central vertical passage 18. The acute angle will be the angle between the perpendicular line and the second line representing the second gas flow passages 38 through the inner diameter of central vertical passage 20 into the central vertical passage 18.

In addition, the first gas flow passages 28 and the second gas flow passages 38 are not required to extend in the same direction or have the same angular orientation relative to the longitudinal axis or centerline 30, and may be in opposite angular directions. The first gas flow passages 28 and the second gas flow passages 38 provide an increase in the available surface area for heat transfer from the heating element 14 onto the gases to be heated improving heating efficiency, provide for a more consistent heat transfer to sheathing material 90 and catheter body 88 and improving the quality of a manufacture of the catheter 22. The first gas flow passages 28 and the second gas flow passages 38 also improve temperature regulation for the gas to be heated, and provide for gas turbulence and a chimney gas flow effect, which in turn disburses heat more evenly across the sheathing material 90 and catheter body 88 improving the quality of a manufacture of the catheter 22. Turbulence for gas present in the central vertical passage 18 creates a more efficient convective heat transfer to the sheathing material 90 and catheter body 88, as compared to a smooth bore semi-laminar flow heating element.

In at least one embodiment, establishment of a turbulent heated gas flow proximate to the sheathing material 90 and catheter body 88 within the central vertical passage 18 facilitates the even adhering of the polymers onto the catheter 22. The chimney gas effect established by the first gas flow passages 28 and the second gas flow passages 38 provide for the turbulent heated gas flow within the central vertical passage 18, and proximate to the sheathing material 90 and catheter body 88. Heated gas may enter into the central vertical passage 18 at a plurality, and at any number of desired locations on the heating element 14, passing upwardly in the central vertical passage 18. As the heated gas moves upwardly in the central vertical passage 18 the heated gas will encounter additional heated gas having a higher temperature, The contact between the heated gas having a lower temperature and the heated gas having a higher relative temperature will cause the turbulence between the two gas temperatures to effectuate thermal transfer for the gas to a consistent median temperature. Diameters/cross sectional areas and number of first gas flow passages 28 and the second gas flow passages 38 and their placement may be varied to achieve more or less turbulence and distribution of waste heat along the length of central vertical passage 18.

Heated gas is not forced through the first gas flow passages 28 or second gas flow passages 38 but occurs naturally through a chimney gas flow effect. Establishment of a turbulent gas flow within the central vertical passage 18 improves control of the temperature and the rate of heat transfer from the heated gas onto the catheter body 88 and sheathing material 90.

In at least one embodiment, FIG. 13 is an exploded detail view of the sealing discs of the iris/variable orifice 36. Each of the sealing discs 40 preferably include a plurality of disc positioning apertures 94. A disc positioning/fastening element 96 passes through each set of aligned disc positioning apertures 94, even though only a single disc positioning/fastening element 96 is shown in FIG. 13. The disc positioning/fastening element 96 is also used to attach the sealing discs 40 to both of the coupler 80 and the bottom plate 62 as positioned therebetween. The sealing discs 40 also include a plurality of slits 98 passing through the center of each of the sealing discs 40. The slits 98 permit the center of the sealing discs 40 to separate, bend and conform in flush contact with the exterior surface of the sheathing 90 passing through each of the sealing discs 40.

Each of the sealing discs 40 are preferably formed of a flexible plastic, polymer, Teflon®, acetal, acrylic, acrylonitrile-butadiene-styrene (ABS), alkyd resins, butadiene, cellulose, cellulose acetate, engineered plastic, epoxy resin, fluroplastic, foam plastic, foam rubber, furane, isoprene, latex, nylon, phenolic resin, phenoxy, phenylene oxide, polycarbonate, polyester, polyacetal, polyethylene, polyimide, polyethylene oxide (PPO), polypropylene, polystyrene, polysulfone, polyurethane, polyvinylchloride (PVC), Polyether ether ketone (PEEK), rubber, silicone resin, styrene, thermoplastic, thermosets, urethanes, vinyl chloride and combinations thereof.

In at least one embodiment, each of the sealing discs 40 are identical with respect to the disc positioning apertures 94 and slits 98. Each adjacent sealing disc 40 is not required to be formed of the same material and the material for each sealing disc 40 may be independently selected creating a restrictive gas passage greatly reducing gas at ambient temperature from entering the central vertical passage 18 through the bottom plate 62 and coupler 80 during the formation of the catheter 22.

In a preferred embodiment, each of the sealing discs 40 has a primary slit 100. The primary slit 100 is aligned with respect to one of the disc positioning apertures 94. The other slits 98 are not necessarily aligned with a disc positioning aperture 94. Each of the sealing discs 40 include the identical, odd number of slits 98. The use of an odd number of slits 98 provides that no slit 98 on a sealing disc 40 will align with another slit 98 on an adjacent or slits on subsequent discs in a set of four sealing discs 40 provided that the adjacent sealing disc 40 has been rotated or offset relative to the original or another sealing disc 40 as described herein. The contact between the sealing disc tip and sealing disc faces proximate to the tips forms a semi-conic shape which flexes with changes in catheter diameter. This dynamic interface minimizes passage of gas at ambient temperature from entering into the central vertical passage 18.

In a first sealing disc 40, the primary slit 100 may be positioned in an upward or north direction. An adjacent or second sealing disc 40 will preferably have the primary slit 100 positioned in an alternative direction, which may be downward or south, right or east, or left or west. A next adjacent sealing disc 40 will preferably have the primary slit 100 positioned in an alternative direction relative to the first two sealing discs 40. Likewise in the fourth sealing disc the primary slit 100 will be placed in a direction which is different from the first three sealing discs 40.

In FIG. 13 the primary slit 100 on the first sealing discs 40 viewed from left to right is positioned in the upper or north direction. In the second sealing disc 40 the primary slit 100 is positioned in the downward or south direction. In the third sealing disc 40 the primary slit 100 is positioned in the left or west direction and in the fourth sealing disc 40 the primary slit 100 is positioned in the right or east direction.

It should be noted that the direction selected for the primary slit 100 on any sealing disc 40 may be in any direction, and adjacent sealing discs 40 forming the iris/variable orifice 36 may be in any direction which is not in alignment to another or adjacent sealing disc 40. For example a set of four sealing discs 40 may have the respective primary slits 100 positioned in the downward, right, left and upward direction. In an alternative set of four the sealing discs 40, respective primary slits 100 may be positioned in the left, right, upward and downward directions. In another alternative set of four sealing discs 40, the respective primary slits 100 may be positioned in the upward, right, downward and left directions. The examples identified are for illustrative purposes and are not intended to be restrictive of the alternative configurations for the primary slits 100 of the sealing discs 40 forming the iris/variable orifice 36. The purpose of the alternative alignment of the primary slits 100 on the sealing discs 40 is to restrict ambient gas flow past the iris/variable orifice 36 and into the central vertical passage 18 as passing the catheter body 88 and sheathing 90.

In an alternative embodiment, three sealing discs 40 may be used in the iris/variable orifice 36 where each of the primary slits 100 is placed into a different respective direction consistent with the positioning alternatives identified herein. In yet a further alternative embodiment, five or multiple sealing discs 40 may be used in the iris/variable orifice 36 where each of the primary slits 100 is placed into a different respective direction. For example, in a five sealing discs 40 configuration, the primary slits 100 may be placed in a respective left, right, downward, upward and right direction. In an alternative five sealing discs 40 configuration, the primary slits 100 may be placed into a upward, right, downward, left and upward direction. In an alternative five sealing discs 40 configuration, the primary slits 100 may be placed into a upward, left, downward, upward, and right respective configuration. It should be noted that any desired combination of configurations for placement of the primary slits 100 is acceptable provide that adjacent sealing discs 40 do not have the primary slits 100 aligned relative to each other, and in each set of four or more sealing discs 40 the configuration includes at least one of each of the upward, right, downward and left positioned primary slits 100.

In a preferred embodiment, each sealing disc 40 includes an odd number of slits 98, such that any number of, or plurality of, sealing discs 40 may have the disc positioning apertures 94 placed on a respective disc positioning/fastening element 96, such that no slits 98 of any of the set of sealing disc 40, forming the iris/variable orifice 36, are in alignment relative to another slit 98. This configuration provides minimum ambient air flow through the plurality of sealing discs 40, and past the sealing disc tips and sheathing 90.

Figure 14:
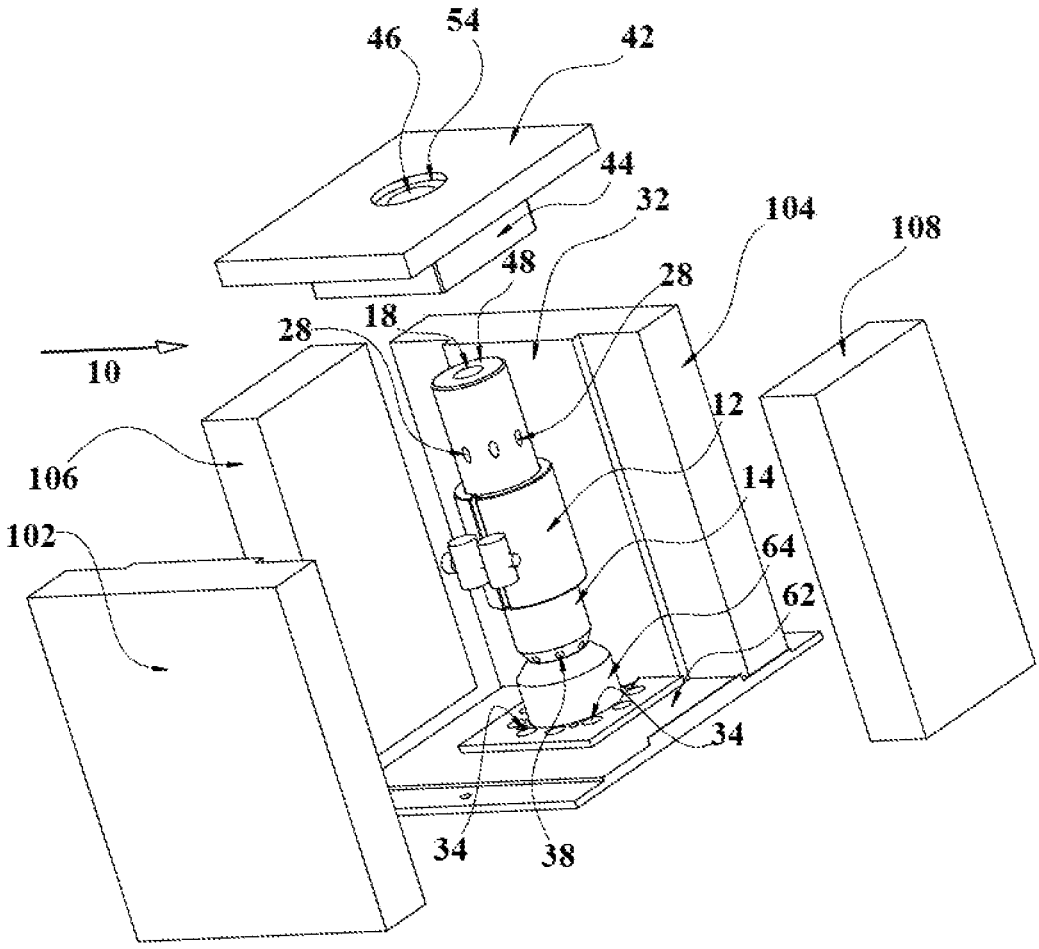
FIG. 14 is a front exploded perspective view of one alternative embodiment of the insulation chamber of the Heater System and Device for Catheter Manufacture.
Figure 15:
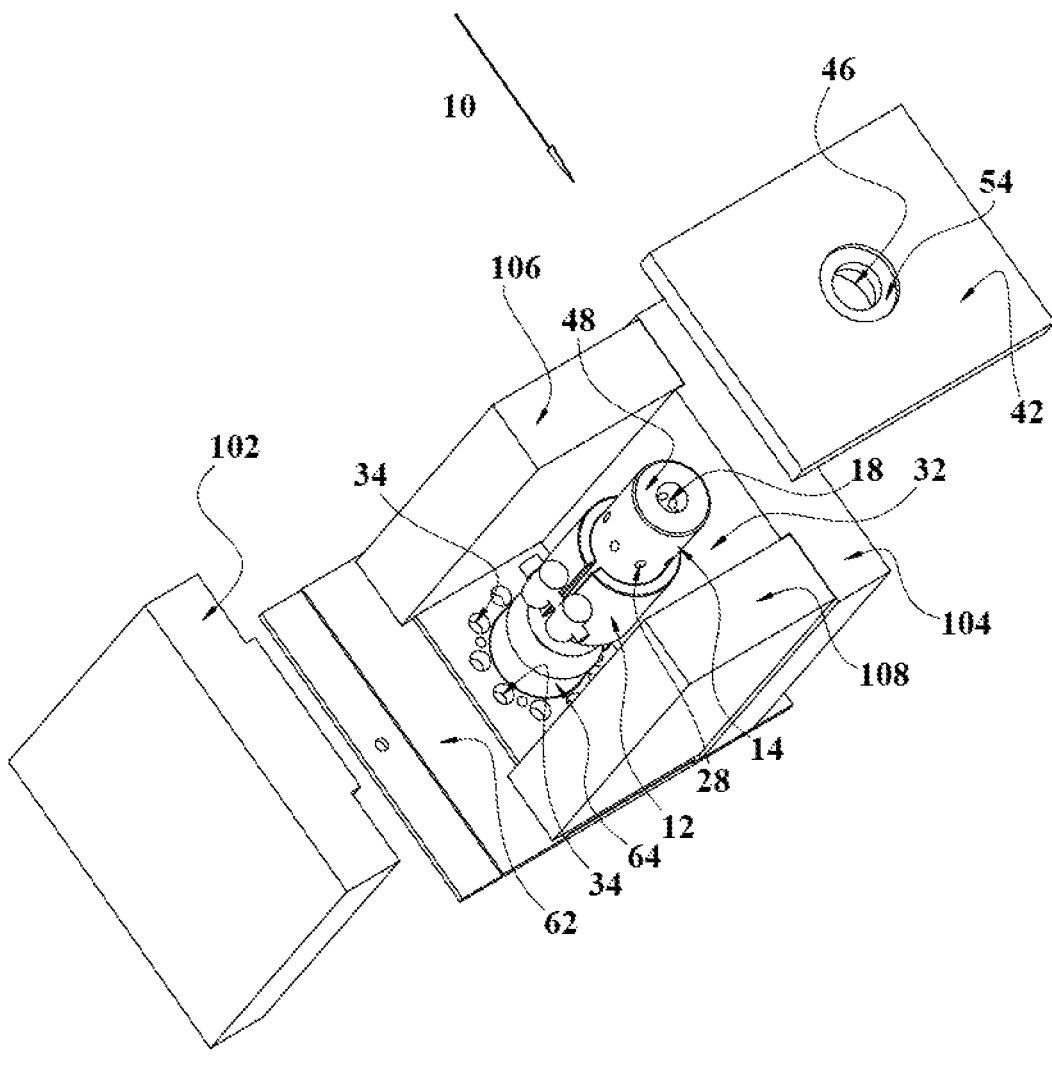
FIG. 15 is a front partial exploded perspective view of one alternative embodiment of the insulation chamber of the Heater System and Device for Catheter Manufacture.
Figure 16:
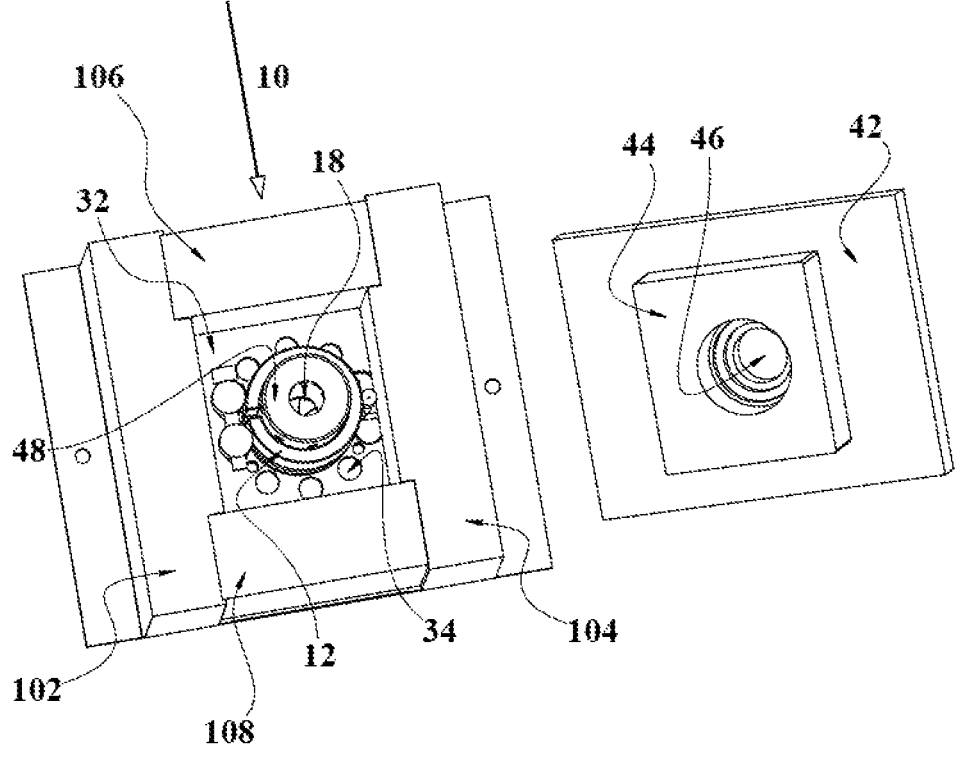
FIG. 16 is a top partial exploded plan view of one alternative embodiment of the insulation chamber of the Heater System and Device for Catheter Manufacture.

In an alternative embodiment as depicted in FIG. 14 through FIG. 16, the Heater System and Device for Catheter Manufacture 10 as located within the insulation chamber 32 is shown. In FIG. 14 through FIG. 16 the Heater System and Device for Catheter Manufacture 10 includes the top plate gas outflow opening 46, circular recess 54, top plate 42, interface structure 44, upper end 48, central vertical passage 18, first gas flow passages 28, thermo-coupling component 12, heating element 14, lower openings 34, second gas flow passages 38, platform 64, and bottom plate 62 as earlier described.

The insulation chamber 32 is preferably formed of an insulated front panel 102, back panel 104, left panel 106 and right panel 108 as releasably engaged to the top plate 42 and the bottom plate 62 as well as two adjacent insulated panels. The insulation chamber 32 is generally rectangular in shape. Each of the front panel 102 and back panel 104 may include a raised middle structure to define opposite ledges to assist in the correct positioning of a left panel 106 and right panel 108 in the opposite ledges.

The front panel 102, back panel 104, left panel 106, and right panel 108 are preferably formed of thermal insulative materials to retain heat within the interior of the insulation chamber 32 following assembly and use of the Heater System and Device for Catheter Manufacture 10. The front panel 102, back panel 104, left panel 106, and right panel 108 are also preferably formed of materials preventing passage of ambient temperature gas into a insulation chamber 32, or the passing of heated gas out of the insulation chamber 32, into the surrounding environment as waste heat. The connecting exterior or interior vertical joints/edges between the front panel 102 and left panel 106, the left panel 106 and the back panel 104, the back panel 104 and the right panel 108, and the right panel 108 and the front panel 102 may be sealed with a suitable tape or setting adhesive to prevent ambient gas entry, or more importantly, waste heated gas from escaping the insulation chamber 32. The heated gas within the insulation chamber 32 exits through the top plate gas outflow opening 46 as aligned with the central vertical passage 18.

FIG. 14 shows the front panel 102, back panel 104, left panel 106, and right panel 108 in an exploded view where only the back panel 104 is positioned in engagement with the bottom plate 62. The front panel 102, back panel 104, left panel 106 and right panel 108 have not as yet been positioned for engagement to the top plate 42, and the front panel 102, left panel 106 and right panel 108 have not been positioned for engagement to the bottom plate 62 or to each other.

FIG. 15 shows the back panel 104, left panel 106, and right panel 108 engaged to the bottom plate 62. The front panel 102 has not as yet been engaged to the other insulated panels, the bottom plate 62 or the top plate 42 to form the insulation chamber 32. FIG. 16 shows the front panel 102, back panel 104, left panel 106, and right panel 108 to be engaged to each other and to the bottom plate 62. The top plate 42 has not as yet been engaged to the insulated panels to form the insulation chamber 32.

Mechanical fastening elements may be used to releasably secure the front panel 102, back panel 104, left panel 106 and right panel 108 to each other and to the bottom plate 62 as well as the top plate 42.

In one alternative embodiment, external structural panels may be disposed exterior to the insulation chamber 32. The external structural panels may be secured to bottom plate 62 and engaged to a catheter manufacturing frame. The external structural panels do not form the interior of insulation chamber 32. The external structural panels may be in contact with the exterior of the front panel 102 and the back panel 104. The external structural panels may be used to provide a perpendicular force against the front panel 102 and the back panel 104 to squeeze the front panel 102 and the back panel 104 together. The left panel 106 and the right panel 108 are located to the interior of the outer edge of the front panel 102 and the back panel 104 respectively. The perpendicular force exerted by the external structural panels bring the front panel 102 and the back panel 104 into secure-intimate contact with exterior contacting panels of the left panel 106 and right panel 108 respectively. The perpendicular force exerted by the external structural panels connect the exterior joints of the front panel 102, back panel 104, left panel 106 and right panel 108 creating a seal and establishing the insulation chamber 32. The exterior corner vertical edges of the front panel 102, back panel 104, left panel 106 and right panel 108 as secured together may also be sealed with a suitable tape or setting adhesive to further prevent ambient gas entry, or more importantly waste heated air from escaping from the interior of insulation chamber 32. Mechanical fastening elements may include, but are not necessarily limited to, screws, bolts within threaded apertures, bolts and nuts, press-fit pins or rods, rivets, nails, clips, brackets, tape, adhesive, or any other attachment or fastening device/method which may be suitable for a particular application or material.

Figure 17:
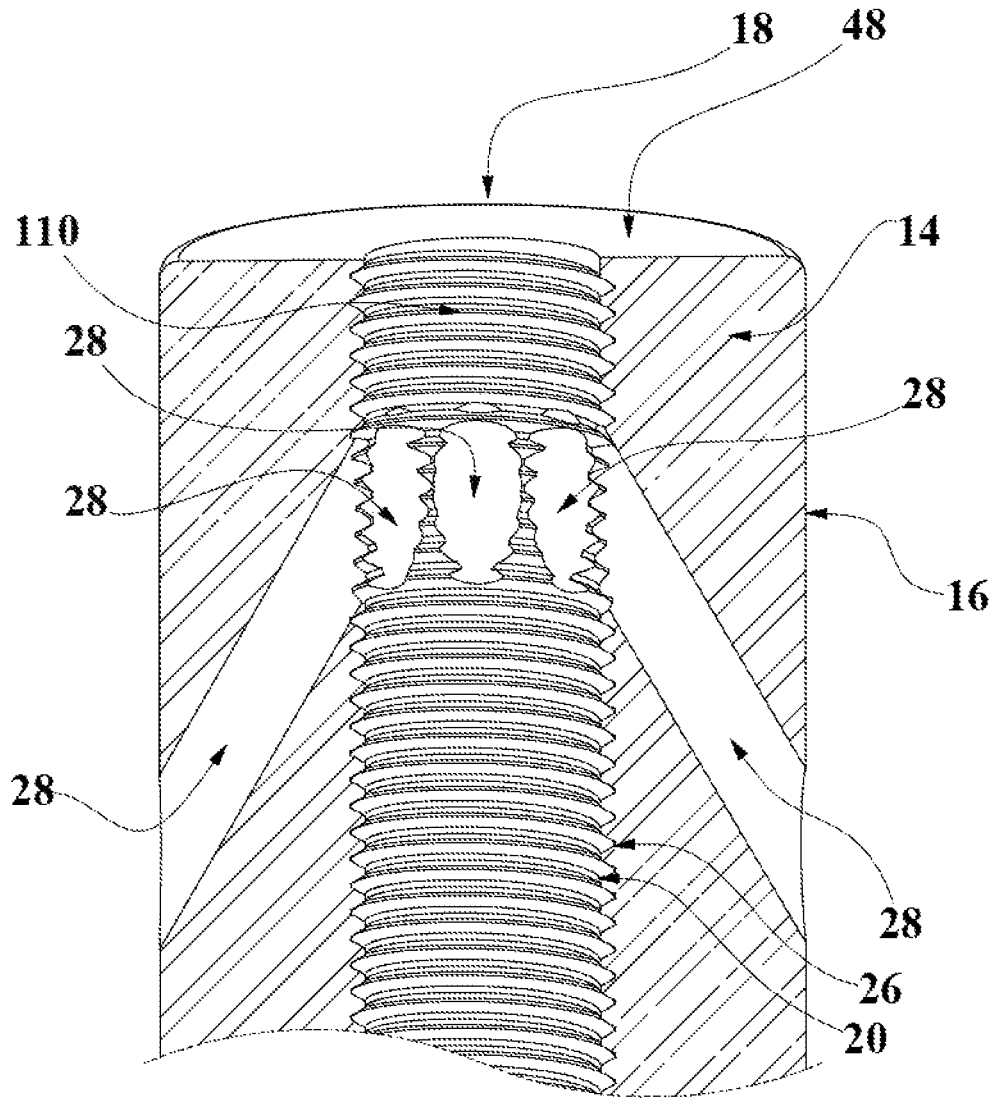
FIG. 17 is a partial detail cross-sectional side view of one alternative embodiment of the surface area increasing geometries of the heating element taken along the line 6-6 of FIG. 2.

In at least one embodiment, as may be seen in FIG. 17, the interior of the central vertical passage 18 includes surface area increasing geometries 26. The surface area increasing geometries 26 may partially or completely cover the surface of the central vertical passage 18. In FIG. 17 the surface area increasing geometries 26 are shown as threads 110, or a threaded surface. The threads 110 increase the surface area of the central vertical passage 18 as opposed to a smooth bore. The provision of increased surface area facilitates exposure of gas to the heated surface area increasing geometries 26, and the transfer of heat to the gas. A desired heat profile within the central vertical passage 18 may be obtained by the provision of different sections, areas, types, or structure for the surface area increasing geometries 26. The heating efficiency for the Heater System and Device for Catheter Manufacture 10 is improved by the inclusion of surface area increasing geometries 26 within the central vertical passage 18 for thermal transfer of heat from the heating element 14 to the gas, as further transferred from the gas onto the sheathing material 90 and catheter body 88.

Figure 18:
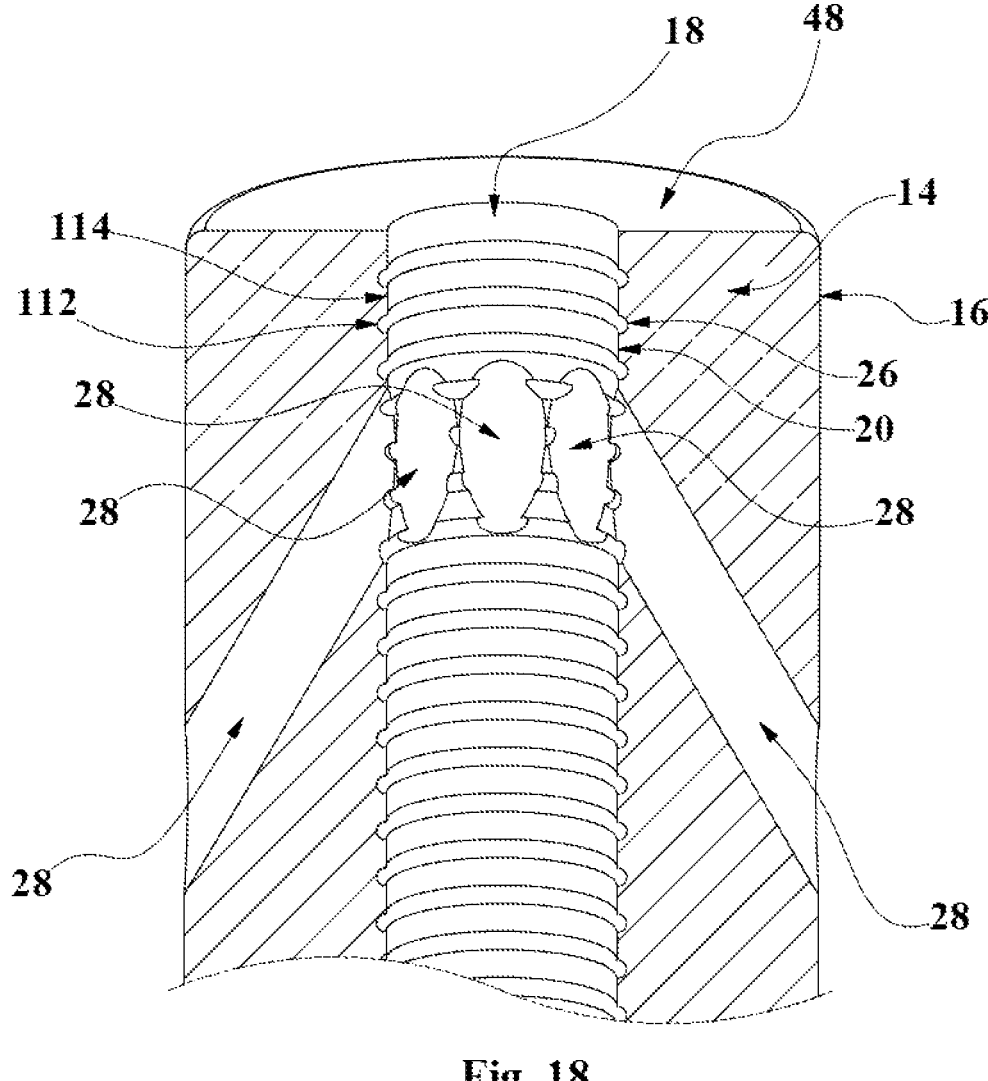
FIG. 18 is a partial detail cross-sectional side view of one alternative embodiment of the surface area increasing geometries of the heating element taken along the line 6-6 of FIG. 2.

In at least one embodiment, as may be seen in FIG. 18, the surface area increasing geometries 26 may be formed of a repetitive pattern of alternating channels 112 and raised surfaces 114. As may be seen in FIG. 19, the surface area increasing geometries 26 may be formed of a repetitive series of adjacent angular shaped grooves 116.

Figure 19:
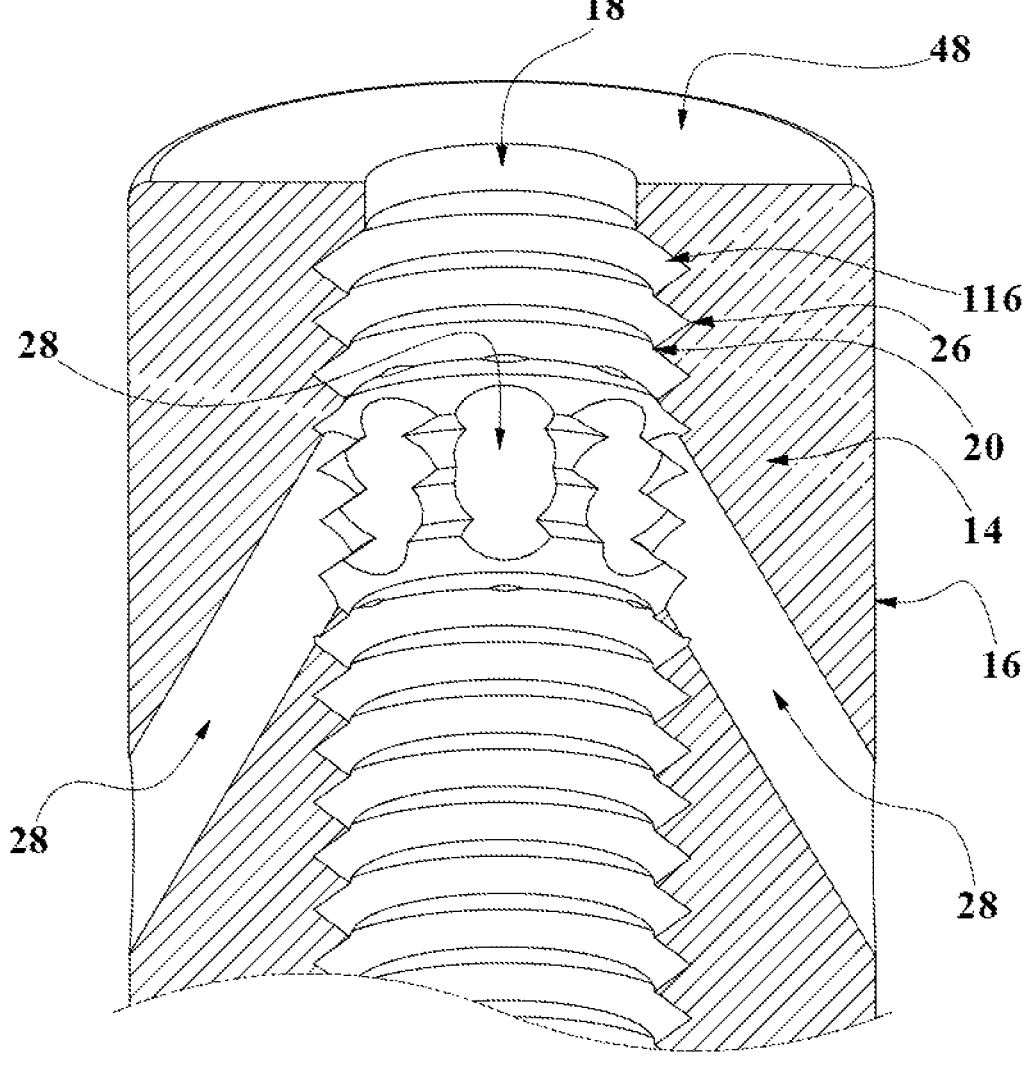
FIG. 19 is a partial detail cross-sectional side view of one alternative embodiment of the surface area increasing geometries of the heating element taken along the line 6-6 of FIG. 2.

The examples of surface area increasing geometries 26 as identified in FIG. 17 through FIG. 19 constitute a very limited number of available structures which may be incorporated into the interior of central vertical passage 18 to increase the surface area for heat transfer onto gas to be heated. Other types of structure may be used to form the surface area increasing geometries 26 including the use of arcuate, concave, convex, flat, angular, round, rectangular, triangular, scales, mesh, other geometric forms or patterns, as well as any other shaped surfaces, or combination of surfaces, as required to establish a heat profile for a particular application. In an alternative embodiment at least a portion of the outer diameter of heating element 16 may include surface area increasing geometries 26 as described herein. The various area increasing geometries 26 are also intended to disrupt laminar flow and generate turbulence.

In an alternative embodiment at least a portion of the outer diameter of heating element 16 may include surface area increasing geometries 26 as described herein.

In at least one alternative embodiment, surface area increasing geometries 26 as previously described and as incorporated by reference herein, may be incorporated into the interior of the first gas flow passages 28 and/or the second gas flow passages 38 simultaneously with, or in substitution for, the inclusion of the surface area increasing geometries 26 within the central vertical passage 18. Additionally, the surface area increasing geometries 26 may be incorporated into the interior or exterior of any extension tubes in communication with the first gas flow passages 28 and/or the second gas flow passages 38. The description herein relate to the first gas flow passages 28 and/or the second gas flow passages 38 surface area increasing geometries 26 is equally applicable to the extension tubes.

Alternatively, the use of surface area increasing geometries 26 within the interior of the central vertical passage 18, the first gas flow passages 28 or the second gas flow passages 38 individually, or in any combination, is not required during the manufacture of a catheter 22.

During the manufacturing process, the Heater System and Device for Catheter Manufacture 10 is moved in an downward direction with respect to the sheathing material 90 and catheter body 88 as disposed centrally through the central vertical passage 18. The sheathing material 90 and catheter body 88 pass upwardly relative to the Heater System and Device for Catheter Manufacture 10 in the direction opposite to the direction identified by arrow 92 in FIG. 2. The Heater System and Device for Catheter Manufacture 10 moves in a downward direction relative to the sheathing material 90 and catheter body 88, which is indicated by arrow 92.

During decent of the Heater System and Device for Catheter Manufacture 10, the interior portion of the heating element 14 proximate to the second gas flow passages 38, is the general area which provides the initial heat transfer to the sheathing material 90 and the catheter body 88. As downward movement of the Heater System and Device for Catheter Manufacture 10 continues in the direction of arrow 92, the sheathing material 90 and catheter body 88 pass through the central portion of the central vertical passage 18, receiving additional heat transfer from the heated gas. As movement of the Heater System and Device for Catheter Manufacture in the direction of arrow 92 continues, the sheathing material 90 and catheter body 88 are exposed to additional heat transfer from the upper portion of the heating element 14 proximate to the first gas flow passages 28. The formed catheter 22 then passes upwardly through the top plate gas outflow opening 46 ending exposure to direct heat transfer from the heating element 14 but continues heating from hot gas which then dissipates as entrains with ambient air.

In a preferred embodiment the Heater System and Device for Catheter Manufacture 10 reduces cycle times, improves catheter quality and consistency, and reduces operating expenses as compared to know manufacturing devices and methods. The surface area increasing geometries 26 within the central vertical passage 18, in conjunction with the first gas flow passages 28 and second gas flow passages 38 improves the consistency of the heat transfer processing temperature over the length of the central vertical passage 18. The dimensions for heating element 14 and for central vertical passage 18 are of sufficient size to accommodate the manufacture of a plurality of catheters 22 having different diameter dimensions, without the need to substitute a different sized heating element 14 for a different catheter 22 diameter dimension.

In at least one embodiment, the inclusion of the insulation chamber 32, central vertical passage 18, the option of surface area increasing geometries 26 within the central vertical passage 18, the first gas flow passages 28, the second gas flow passages 38, and the option of the inclusion of surface area increasing geometries 26 within either the first gas flow passages 28 or the second gas flow passages 38, within the heating element 14, minimizes waste of thermal energy leading to reduced operational cost during the manufacture of a catheter 22.

In at least one embodiment, the heating element 14 is formed of copper alloy material. In the past the air heated by the heating element and band heater is dissipated into a surrounding room in most reflow machines. As disclosed herein, the insulated front panel 102, back panel 104, left panel 106, and right panel 108 are positioned in surrounding engagement relative to the heating element 14. The insulation chamber 32 captures the gas heated by the exterior of the thermo-coupling component 12 and the heating element 14. Ambient temperature gas may enter into the insulation chamber 32 through the lower openings 34, where previously heated gas by the exterior surface of the thermo-coupling component 12 and the heating element 14 is already present.

Previously heated gas within the insulation chamber 32 may escape from the insulation chamber 32 into the first gas flow passages 28 or the second gas flow passages 38 and into the central vertical passage 18 for exit through the top plate gas outflow opening 46. The gas entering the insulation chamber 32 through the lower openings 34, as well as the wire guide 60, is heated by the exterior of the thermo-coupling component 12 and the heating element 14. The pre-heated gas is also disbursed in the insulation chamber 32, and is cooled by additional gas entering the insulation chamber 32 through the lower openings 34 and wire guide 60.

Heat from the exterior of the thermo-coupling component 12 and the heating element 14 continues to heat all gas within the interior of the insulation chamber 32. Gas heated by the exterior of the thermo-coupling component 12 and the heating element 14, as within the insulation chamber 32, then enters the first gas flow passages 28 and the second gas flow passages 38 into the central vertical passage 18. Gas in the first gas flow passages 28, second gas flow passages 38 and central vertical passage 18 is further heated by the interior surfaces of the first gas flow passages 28, second gas flow passages 38 and central vertical passage 18. Heated gas in the central vertical passage 18 is exposed to the sheathing material 90, which shrinks and seals relative to the catheter body 88 as the heating element 14 is lowered in the direction of arrow 92. As the heated gas passes the sheathing material 90 heat from the gas is transferred to the sheathing material 90 causing the constriction of the sheathing material 90 relative to the catheter body 88. When intimate contact is established between sheathing material 90 and the outer layers of catheter body 88, heat energy from the central vertical passage 18 is transferred through sheathing material 90, compressing it further, and to the layers of catheter body 88, which are heated, compressed and bonded to the layers they are in intimate contact with. The heated gas then exits the central vertical passage 18 proximate to the top plate gas outflow opening 46, which is the primary gas flow passage from the interior of the insulation chamber 32 through first gas flow passages 28, second gas flow passages 38. It should be noted that the configuration of the front panel 102, back panel 104, left panel 106, and right panel 108 relative to the top plate 42 and the bottom plate 62 significantly restrict gas exit from the insulation chamber 32, with the exception of exit through the top plate 42 gas outflow opening 46.

In at least one embodiment, the platform 64 elevates and insulates the heating element 14 from contact with the bottom plate 62. The thermal separation of the heating element 14 from the bottom plate 62 enables bottom plate 62 to remain at or near ambient air temperature which possess no harm to personnel in an inadvertent contact with bottom plate 62. The platform 64 elevates the heating element 14 higher into the insulation chamber 32 and further from incoming ambient air which positions gas flow passages 38 to intake preheated gas from insulation chamber 32 which is not at ambient temperature.

The receiving guide 56 in the interface structure 44 may be insulated and position the upper end 48 of the heating element 14 relative to the top plate 42. The receiving guide 56 also centers the central vertical passage 18 relative to the top plate gas outflow opening 46 establishing a restrictive gas passage between the top of the heating element 14 and the top plate 42 to prevent loss of heated gas from the interior of the insulation chamber 32.

In a preferred embodiment the first gas flow passages 28, second gas flow passages 38 and central vertical passage 18 increase the surface area for, and the working length of, the heating element 14.

Heated gas exiting the top plate gas outflow opening 46 rapidly mixes with ambient temperature gas which cools the heated gas rapidly. The interface structure 44 and the receiving guide 56 may include an increased thickness dimension which in turn functions to extend the length of sheathing 90 exposed to turbulent air at a desired processing temperature and to provide a non-heated surface proximate to the top plate 42. The insulated receiving guide 56 above the top of the heating element 14 does not add heat energy to the gas, and does function to restrict or prevent the heated gas in the central vertical passage 18 from being dispersed/cooled by ambient room air.

In at least one embodiment, a second iris/variable orifice 36 may be added to the circular recess 54, and receiving guide 56 in order to further to restrict gas flow from the insulation chamber 32. The restriction of gas flow through the first gas flow passages 28, second gas flow passages 38 and central vertical passage 18 improves the efficiency of the catheter formation process and increases the effective length for processing the catheter 22.

The iris/variable orifice 36 around the catheter 22 establishes a gas passage restriction relative to the lower portion of the heating element 14. The gas passage restriction created by the iris/variable orifice 36 continues to restrict gas exit from the central vertical passage 18 as the catheter body 88 and the sheathing material 90 passes upwardly through the iris/variable orifice 36 during manufacture of the catheter 22.

The restriction of the gas flow by the iris/variable orifice 36 around the catheter body 88 and the sheathing material 90, in conjunction with the first gas flow passages 28, second gas flow passages 38 and central vertical passage 18, regulates the volume of gas entering into the central vertical passage 18, and due to the increased heating surface area provided by the central vertical passage 18, first gas flow passages 28 and second gas flow passages 38 improves heat transfer onto the catheter body 88 and sheathing material 90. The combination of heated gas in the insulation chamber 32, with additional heat exposure to the gas passing through the first gas flow passages 28, second gas flow passages 38 and central vertical passage 18, increases the effective processing length of the heating element 14.

In at least one embodiment, the catheter body 88 and sheathing material 90 are stationary relative to a frame and the insulation chamber 32, and the heating element 14 moves downwardly relative to the stationary catheter body 88 and sheathing material 90 to form the catheter 22. The catheter body 88, sheathing material 90 are centrally positioned within, and disposed vertically, relative to the central vertical passage 18. The inner surface of one or more of the central vertical passage 18, first gas flow passages 28 and second gas flow passages 38, may include surface area increasing geometries 26 to increase surface area for heat transfer onto the catheter body 88 and sheathing material 90.

The surface area increasing geometries 26 may be incorporated onto or into the central vertical passage 18, first gas flow passages 28 and/or second gas flow passages 38 through use of tapping, an electric discharge machine, the provision of traditionally machined features, or cast features, or three dimensional printed metal in order to increase the surface area of the central vertical passage 18, first gas flow passages 28 and/or second gas flow passages 38.

In some embodiments, the diameter dimension for the heating element 14 may be between ¾ inch and 1 inch. In other embodiments the diameter dimension for the heating element 14 may be less than ¾ inch or larger than 1 inch. In some embodiments, the length dimension for the heating element 14 may be between 3 inches and 4 inches. In other embodiments, the length dimension for the heating element 14 may be less than 3 inches or larger than 4 inches. In some embodiments, the length dimension for the heating element 14 has an impact on processing speeds of catheter 22 formation, where a shorter length dimension for the heating element 14 may reduce required processing times.

In a first embodiment, the heating assembly for a catheter manufacture machine, includes an elongate heating element having an outer diameter, a central vertical passage, an upper end and a lower end, the heating element has a longitudinal axis, the central vertical passage extends in the direction of the longitudinal axis, the central vertical passage is centrally disposed relative to the heating element traversing the upper end and the lower end, and a plurality of first gas flow passages traverse the heating element, the first gas flow passages extend from the outer diameter of heating element at an angle relative to the longitudinal axis traversing an inner diameter of the central vertical passage proximate to the upper end, wherein the first gas flow passages traversing the outer diameter are constructed and arranged as a gas inlet, and the first gas flow passages traversing the inner diameter of central vertical passage are constructed and arranged as a gas outlet for gas into the central vertical passage, the inner diameter of the central vertical passage being in communication with the first gas flow passages traversing the outer diameter of heating element at a first distance from the upper end which is larger than a second distance between the first gas flow passages traversing the inner diameter of central vertical passage and the upper end, the first gas flow passages being further constructed and arranged for passage of previously heated gas exterior to the heating element into the central vertical passage.

In a second alternative embodiment according to the first embodiment, the heating element further comprises a plurality of second gas flow passages traversing the heating element, the second gas flow passages extending from the outer diameter of heating element at an angle relative to the longitudinal axis traversing the inner diameter of central vertical passage proximate to the lower end.

In a third alternative embodiment according to the second embodiment, the second gas flow passages traversing the outer diameter of heating element are constructed and arranged as a second gas inlet and the second gas flow passages traversing the inner diameter of central vertical passage are constructed as a second gas outlet into the central vertical passage, the second gas flow passages traversing the outer diameter of the heating element at a third distance from the lower end which is smaller than a fourth distance between the second gas flow passages traversing the inner diameter of central vertical passage and the lower end, the second gas flow passages being further constructed and arranged for passage of the previously heated gas exterior to the heating element into the central vertical passage.

In a fourth alternative embodiment according to the third embodiment, at least one of the central vertical passage, the first gas flow passages and the second gas flow passages comprise surface area increasing geometries.

In a fifth alternative embodiment according to the fourth embodiment, the heating element is formed of copper alloy material.

In a sixth alternative embodiment according to the fifth embodiment, the heating assembly further includes an iris/variable orifice positioned below the lower end.

In a seventh alternative embodiment according to the sixth embodiment, the iris/variable orifice comprises a plurality of sealing discs, each of the sealing discs having a plurality of centrally located slits and a primary slit.

In an eighth alternative embodiment according to the seventh embodiment, the primary slit on a first sealing disc is positioned in a first direction and the primary slit on a second sealing disc is positioned at a second direction offset relative to the first direction.

In a ninth alternative embodiment according to the eighth embodiment, the primary slit on a third sealing disc is positioned in a third direction, the third direction being offset relative to the first direction and the second direction.

In a tenth alternative embodiment according to the ninth embodiment, the iris/variable orifice restricts gas at ambient temperature from entering into said central vertical passage.

In an eleventh alternative embodiment according to the tenth embodiment, the catheter body and sheathing material are centrally disposed along the longitudinal axis within the central vertical passage and the catheter body and the sheathing material pass centrally through the iris/variable orifice.

In a twelfth alternative embodiment according to the eleventh embodiment, the heater assembly further comprises an insulation chamber having a insulation chamber interior, the heating element is centrally positioned in the insulation chamber interior.

In a thirteenth alternative embodiment according to the twelfth embodiment, the insulation chamber comprises a front panel, a rear panel, a left panel, and a right panel extending upwardly from a bottom plate, the bottom plate supporting the heating element.

In a fourteenth alternative embodiment according to the thirteenth embodiment, the bottom plate has a centrally located bottom plate catheter orifice, wherein the catheter body and the sheathing material enter the central vertical passage and the bottom plate catheter orifice.

In a fifteenth alternative embodiment according to the fourteenth embodiment, the insulation chamber has a top plate which in turn has an interface structure, the top plate and the interface structure having a centrally aligned top plate gas outflow opening, wherein the catheter body and the sheathing material exit the central vertical passage through the top plate gas outflow opening.

In a sixteenth alternative embodiment according to the fifteenth embodiment, the bottom plate has a plurality of lower openings.

In a seventeenth alternative embodiment according to the sixteenth embodiment, the iris/variable orifice is disposed below and is in contact with the bottom plate proximate to the bottom plate catheter orifice.

In an eighteenth alternative embodiment according to the seventeenth embodiment, the bottom plate, the front panel, the rear panel, the left panel, the right panel and the top plate restrict the passage of previously heated gas disposed in the insulation chamber interior for passage into the first gas flow passages and the second gas flow passages for inflow into the central vertical passage.

The illustrations of the embodiments described herein are intended to provide a general understanding of the structure of the various embodiments. The illustrations are not intended to serve as a complete description of all of the elements and features of apparatus and systems that utilize the structures or methods described herein.

Many other embodiments may be apparent to those of skill in the art upon reviewing the disclosure. Other embodiments may be utilized and derived from the disclosure, such that structural and logical substitutions and changes may be made without departing from the scope of the disclosure. Additionally, the illustrations are merely representational and may not be drawn to scale. Certain proportions within the illustrations may be exaggerated, while other proportions may be minimized.

Accordingly, the disclosure and the figures are to be regarded as illustrative rather than restrictive. While this specification contains many specifics, these should not be construed as limitations on the scope of the invention or of what may be claimed, but rather as descriptions of features specific to particular embodiments of the invention. Certain features that are described in this specification in the context of separate embodiments can also be implemented in combination in a single embodiment.

Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

Similarly, while operations are depicted in the drawings and described herein in a particular order, this should not be understood as requiring that such operations be performed in the particular order shown or in sequential order, or that all illustrated operations be performed, to achieve desirable results. Moreover, the separation of various system components in the embodiments described above should not be understood as requiring such separation in all embodiments, and it should be understood that the described components and systems can generally be integrated together in a single product or packaged into multiple products.

One or more embodiments of the disclosure may be referred to herein, individually and/or collectively, by the term "invention' merely for convenience and without intending to voluntarily limit the scope of this application to any particular invention or inventive concept. Moreover, although specific embodiments have been illustrated and described herein, it should be appreciated that any subsequent arrangement designed to achieve the same or similar purpose may be substituted for the specific embodiments shown. This disclosure is intended to cover any and all subsequent adaptations or variations of various embodiments.

Combinations of the above embodiments, and other embodiments not specifically described herein, are apparent to those of skill in the art upon reviewing the description. It is intended that the foregoing detailed description be regarded as illustrative rather than limiting and that it is understood that the following claims including all equivalents are intended to define the scope of the invention.

The claims should not be read as limited to the described order or elements unless stated to that effect. Therefore, all embodiments that come within the scope and spirit of the following claims and equivalents thereto are claimed as the invention.

While the foregoing is a description of the preferred embodiments for carrying out the invention for the purposes of complying with 37 C.F.R. 1.72, it is also intended in an illustrative rather than a restrictive sense. Variations to the exact embodiment described may be apparent to those skilled in such equipment without departing from the spirit and scope of the invention as defined by the claims set out below.

This completes the description of the preferred and alternate embodiments of the invention. Those skilled in the art may recognize other equivalents to the specific embodiment described herein which equivalents are intended to be encompassed by the claims attached hereto.

The above disclosure is intended to be illustrative and not exhaustive. This description will suggest many variations and alternatives to one of ordinary skill in this art. The various elements shown in the individual figures and described above may be combined or modified for combination as desired. All these alternatives and variations are intended to be included within the scope of the claims where the term "comprising" means "including, but not limited to".

These and other embodiments which characterize the invention are pointed out with particularity in the claims annexed hereto and forming a part hereof. However, for further understanding of the invention, its advantages and objectives obtained by its use, reference should be made to the drawings which form a further part hereof and the accompanying descriptive matter, in which there is illustrated and described embodiments of the invention.

I claim:

1. A heating assembly for a catheter manufacture machine, said heating assembly comprising:

an elongate heating element having a outer diameter, a central vertical passage, an upper end and a lower end, said heating element having a longitudinal axis, said central vertical passage extending in the direction of said longitudinal axis, said central vertical passage being centrally disposed relative to said heating element traversing said upper end and said lower end; and a plurality of first gas flow passages traversing said outer diameter, said first gas flow passages extending from said outer diameter at an angle relative to said longitudinal axis traversing an inner diameter of said central vertical passage proximate to said upper end, wherein said first gas flow passages traversing said outer diameter are constructed and arranged as a gas inlet and said first gas flow passages traversing said inner diameter are constructed and arranged as a gas outlet for gas entering into the central vertical passage, said first gas flow passages traversing said outer diameter at a first distance from said upper end which is larger than a second distance between said first gas flow passages traversing said inner diameter and said upper end, said first gas flow passages being further constructed and arranged for passage of previously heated gas exterior to said heating element into said central vertical passage.

2. The heating assembly according to claim 1, said heating element further comprising a plurality of second gas flow passages traversing said outer diameter, said second gas flow passages extending from said outer diameter at an angle relative to said longitudinal axis traversing said inner diameter proximate to said lower end.

3. The heating assembly according to claim 2, wherein said second gas flow passages traversing said outer diameter are constructed and arranged as a second gas inlet and said second gas flow passages traversing said inner diameter are constructed and arranged as a second gas outlet for said gas entering into said central vertical passage, said second gas flow passages traversing said outer diameter at a third distance from said lower end which is smaller than a fourth distance between said second gas flow passages traversing said inner diameter and said lower end, said second gas flow passages being further constructed and arranged for passage of said previously heated gas exterior to said heating element into said central vertical passage.

4. The heating assembly according to claim 3, wherein at least one of said central vertical passage, said first gas flow passages and said second gas flow passages comprising surface area increasing geometries.

5. The heating assembly according to claim 4, wherein said heating element is formed of copper alloy material.

6. The heating assembly according to claim 5, said heating assembly further comprising an iris/variable orifice positioned below said lower end.

7. The heating assembly according to claim 6, said iris/variable orifice comprising a plurality of sealing discs, each of said sealing discs having a plurality of centrally located slits and a primary slit.

8. The heating assembly according to claim 7, wherein said primary slit on a first sealing disc is positioned in a first direction and said primary slit on a second sealing disc is positioned at a second direction offset relative to said first direction.

9. The heating assembly according to claim 8, wherein said primary slit on a third sealing disc is positioned in a third direction, said third direction being offset relative to said first direction and said second direction.

10. The heating assembly according to claim 9, wherein a catheter body and sheathing material are centrally disposed along said longitudinal axis within said central vertical passage and said catheter body and said sheathing material pass centrally through said iris/variable orifice.

11. The heating assembly according to claim 10, said heater assembly further comprising a insulation chamber having a insulation chamber interior, said heating element being positioned in said insulation chamber interior.

12. The heating assembly according to claim 11, said heating assembly further comprising a bottom plate, said insulation chamber comprising a front panel, a rear panel, a left panel, and a right panel extending upwardly from said bottom plate, said bottom plate supporting said heating element.

13. The heating assembly according to claim 12, said bottom plate having a centrally located bottom plate catheter orifice, wherein said catheter body and said sheathing material enter said central vertical passage through said bottom plate catheter orifice.

14. The heating assembly according to claim 13, said heating assembly further comprising a top plate, said top plate having a centrally aligned top plate gas outflow opening, wherein said catheter body and said sheathing material exit said central vertical passage proximate to said top plate gas outflow opening.

15. The heating assembly according to claim 14, said bottom plate having a plurality of lower openings.

16. The heating assembly according to claim 15, wherein said iris/variable orifice is disposed below and is in contact with said bottom plate proximate to said bottom plate catheter orifice.

17. The heating assembly according to claim 16, wherein said insulation chamber restricts escape of heated gas from said insulation chamber interior, said heated gas within said insulation chamber interior entering into said first gas flow passages and said second gas flow passages for inflow into said central vertical passage.

* * * * *